United States Patent
Xu et al.

(10) Patent No.: US 10,526,332 B2
(45) Date of Patent: Jan. 7, 2020

(54) IMIDAZO-PYRIMIDONE COMPOUNDS, AND PREPARATION METHOD AND APPLICATION THEREOF

(71) Applicant: Nanjing Gator Meditech Company, Ltd., Jiangsu (CN)

(72) Inventors: Ruo Xu, Watchung, NJ (US); Yunyong Liu, Jiangsu (CN)

(73) Assignee: Madera Therapeutics, LLC, Cary, NC (US)

( * ) Notice: Subject to any disclaimer, the term of this patent is extended or adjusted under 35 U.S.C. 154(b) by 0 days.

(21) Appl. No.: 15/574,469

(22) PCT Filed: Jun. 17, 2016

(86) PCT No.: PCT/CN2016/086145
§ 371 (c)(1),
(2) Date: Nov. 15, 2017

(87) PCT Pub. No.: WO2016/184437
PCT Pub. Date: Nov. 24, 2016

(65) Prior Publication Data
US 2018/0141946 A1    May 24, 2018

(30) Foreign Application Priority Data
May 15, 2015 (CN) .......................... 2015 1 0250497

(51) Int. Cl.
| C07D 471/14 | (2006.01) |
| C07D 487/14 | (2006.01) |
| A61K 31/519 | (2006.01) |
| A61K 31/5377 | (2006.01) |

(52) U.S. Cl.
CPC .......... *C07D 471/14* (2013.01); *A61K 31/519* (2013.01); *A61K 31/5377* (2013.01); *C07D 487/14* (2013.01)

(58) Field of Classification Search
CPC ............................ C07D 471/14; C07D 487/14
See application file for complete search history.

(56) References Cited

U.S. PATENT DOCUMENTS

| 8,673,923 B2 | 3/2014 | El-Deiry et al. |
| 9,061,032 B2 | 6/2015 | El-Deiry et al. |
| 9,072,744 B1 | 7/2015 | El-Deiry et al. |
| 9,265,765 B2 | 2/2016 | Stogniew et al. |
| 9,376,437 B2 | 6/2016 | Stogniew et al. |
| 9,452,165 B2 | 9/2016 | El-Deiry et al. |
| RE46,290 E | 1/2017 | El-Deiry et al. |
| 9,629,842 B2 | 4/2017 | El-Deiry et al. |
| 9,688,679 B2 | 6/2017 | Stogniew et al. |
| 2012/0276088 A1 | 11/2012 | El-Deiry et al. |
| 2014/0248264 A1 | 9/2014 | El-Deiry et al. |
| 2014/0271540 A1 | 9/2014 | Stogniew et al. |
| 2014/0335048 A1 | 11/2014 | Stogniew et al. |
| 2015/0202206 A1 | 7/2015 | El-Deiry et al. |
| 2015/0265619 A1 | 9/2015 | El-Deiry et al. |
| 2016/0151403 A1 | 6/2016 | El-Deiry |
| 2016/0264574 A1 | 9/2016 | Stogniew et al. |
| 2017/0000790 A1 | 1/2017 | El-Deiry et al. |
| 2017/0096431 A1 | 4/2017 | Allen et al. |
| 2017/0224690 A1 | 8/2017 | Allen et al. |
| 2017/0319587 A1 | 11/2017 | Stogniew et al. |

FOREIGN PATENT DOCUMENTS

| WO | 2014160130 | 10/2014 |
| WO | 2015153468 | 10/2015 |

OTHER PUBLICATIONS

Patani et al. "Bioisosterisnn: A Rational Approach in Drug Design" Chemical Reviews, 1996, vol. 96, pp. 3147-3176.*

* cited by examiner

*Primary Examiner* — Joseph R Kosack
(74) *Attorney, Agent, or Firm* — Lewis Kohn & Walker LLP; David M. Kohn

(57) ABSTRACT

Compounds of formula (I), imidazopyrimidine ketones, as well as preparations and applications thereof. Compounds and pharmaceutically acceptable salts thereof which stimulate the body to produce tumor necrosis factor-related apoptosis-inducing ligands, while avoiding the drawbacks of existing cancer treatments based on recombinant proteins and antibodies. Thus, they can provide novel options for the treatment of related tumors.

(I)

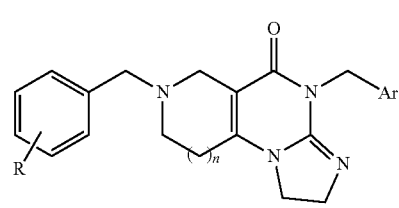

9 Claims, No Drawings

IMIDAZO-PYRIMIDONE COMPOUNDS, AND PREPARATION METHOD AND APPLICATION THEREOF

This application is a United States National Stage Application claiming the benefit of priority under 35 U.S.C. 371 from International Patent Application No. PCT/CN2016/086145 filed Jun. 17, 2016, which claims the benefit of priority from Chinese Patent Application Serial No. CN 201510250497.7 filed May 15, 2015, the entire contents of which are herein incorporated by reference.

TECHNICAL FIELD

The present invention relates to the field of medical technology, in particular to imidazopyrimidinyl ketone compounds, their preparation methods and applications.

BACKGROUND

As a devastating and life threatening disease, cancer has been the focus of tremendous amount of research in the past. As the result of these studies, a variety of cancer therapeutics have been developed with various degree of success. However, all traditional treatments have some limitations that cannot be ignored and more effective and safer treatments are needed by cancer patients. Recently, apoptosis-inducing molecules of tumor cells have attracted attention in the field of cancer therapy. These molecules are tumor necrosis factor-related apoptosis-inducing ligands (TRAIL), which are powerful inhibitors of cancer cells. The biggest advantage of these molecules is that they can selectively induce the apoptosis of tumor cells with no toxic side effects on normal cells. Not only can they induce the apoptosis of nearly two-thirds of tumor cell lines, but also relatively effective on tumor cells that are not sensitive to radiotherapy and chemotherapy. Therefore, TRAIL has gradually become a hot topic in cancer research since their discovery.

At present time, scientists have successfully treated cancer using tumor necrosis factor-related apoptosis-inducing ligands, which come from synthetic recombinant proteins and antibodies. Such recombinant form of soluble TRAIL has shown to induce tumor cell apoptosis. However, it can also simultaneously induce normal liver cell apoptosis. To avoid the toxic side effects, researchers have tried to obtain TRAIL by other means. U.S. Patent US2014/0335048A1 discloses a pharmaceutical composition for the active ingredient (7-benzyl-4-(2-methylbenzyl) 1,2,6,7,8,9-hexahydro-imidazo[1,2-a]pyrido[3,4-e]pyrimidine-5(4H)-one (TIC10), which stimulates the body to produce TRAIL while avoiding the problems of existing recombinant protein and antibody based treatments; however, there are issues regarding its applicability and activity.

SUMMARY OF THE INVENTION

One objective of the present invention is to provide imidazole and pyrimidine ketone compounds that stimulate human TRAIL generation for the treatment of neoplastic diseases.

Another objective of the present invention is to provide methods of preparation for above compounds and pharmaceutically acceptable salts thereof.

A further objective of the present invention is to provide the above-mentioned compounds for use in the development of anti-cancer drugs.

A further objective of the present invention is to provide acceptable salts of aforementioned compounds as active ingredients in pharmaceutical compositions.

To achieve the above purpose, the technical aspects of the present invention are the preparations of the compounds of formula (I), or pharmaceutically acceptable salts thereof,

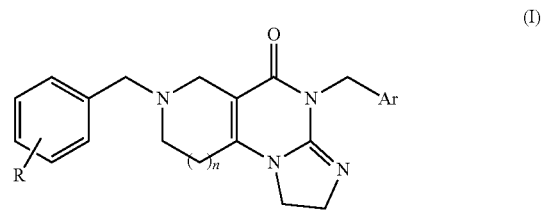

whereas, n=0 or 1, R is H, halogen, C1-6 straight-chain or branched-chain alkyl, C1-6 straight-chain or branched-chain alkoxyl, halo-substituted C1-6 straight-chain or branched-chain alkyl, one or two hetero atoms, such as nitrogen or oxygen, an unsubstituted or substituted six-membered heterocycle alkyl; Ar is mono- or di-substituted aryl groups, the substituents include halo, C1-6 straight-chain or branched-chain alkyl, halo-substituted C1-6 straight-chain or branched-chain alkyl; and when n=1 and R is H, Ar is not phenyl, 2-chlorophenyl, difluorophenyl or ortho-methylphenyl.

Preferably, R is H, halogen, C1-4 straight-chain or branched-chain alkyl, C1-4 straight-chain or branched-chain alkoxy, halo-substituted C1-4 straight-chain or branched-chain alkyl, one or two nitrogen hetero atoms or oxygen hetero atom, an unsubstituted or substituted six-membered heterocycle alkyl; Ar is mono- or di-substituted aryl groups, the substituents include halogen, C1-4 straight-chain or branched-chain alkyl, halo-substituted C1-4 straight-chain or branched-chain alkyl, and when n=1 and R is H, Ar is not phenyl, 2-chlorophenyl, difluorophenyl or o-methylbenzene group.

More preferably, R is F, Cl, Br, methyl, t-butyl, methoxy, trifluoromethyl,

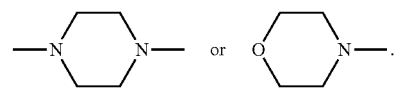

More preferably, Ar is a mono- or di-substituted aryl group, the substituent is F, Cl, one or two methyl or trifluoromethyl, or Br.

The final products in the present invention are prepared according to the following steps:
a. Compound 1 undergoes reduction reaction to obtain compound 2;
b. Compound 2 reacts with an unsubstituted or substituted benzaldehyde to prepare compound 3;
c. Compound 4 reacts with methyl iodide to prepare compound 5;
d. Compound 5 reacts with substituted benzyl amine to prepare compound 6;
e. Compound 7 reacts ethyl acrylate to prepare compound 8;
f. Compound 8 reacts with ethyl bromoacetate to prepare compound 9;
g. Compound 9 undergoes further transformation to prepare compound 10;

h. Finally, compound 10 reacts with compound 6 to give a series of compounds with n=0; and compound 3 reacts with Compound 6 to give a series of compound with n=1.

The following reaction scheme depicts the reaction process:

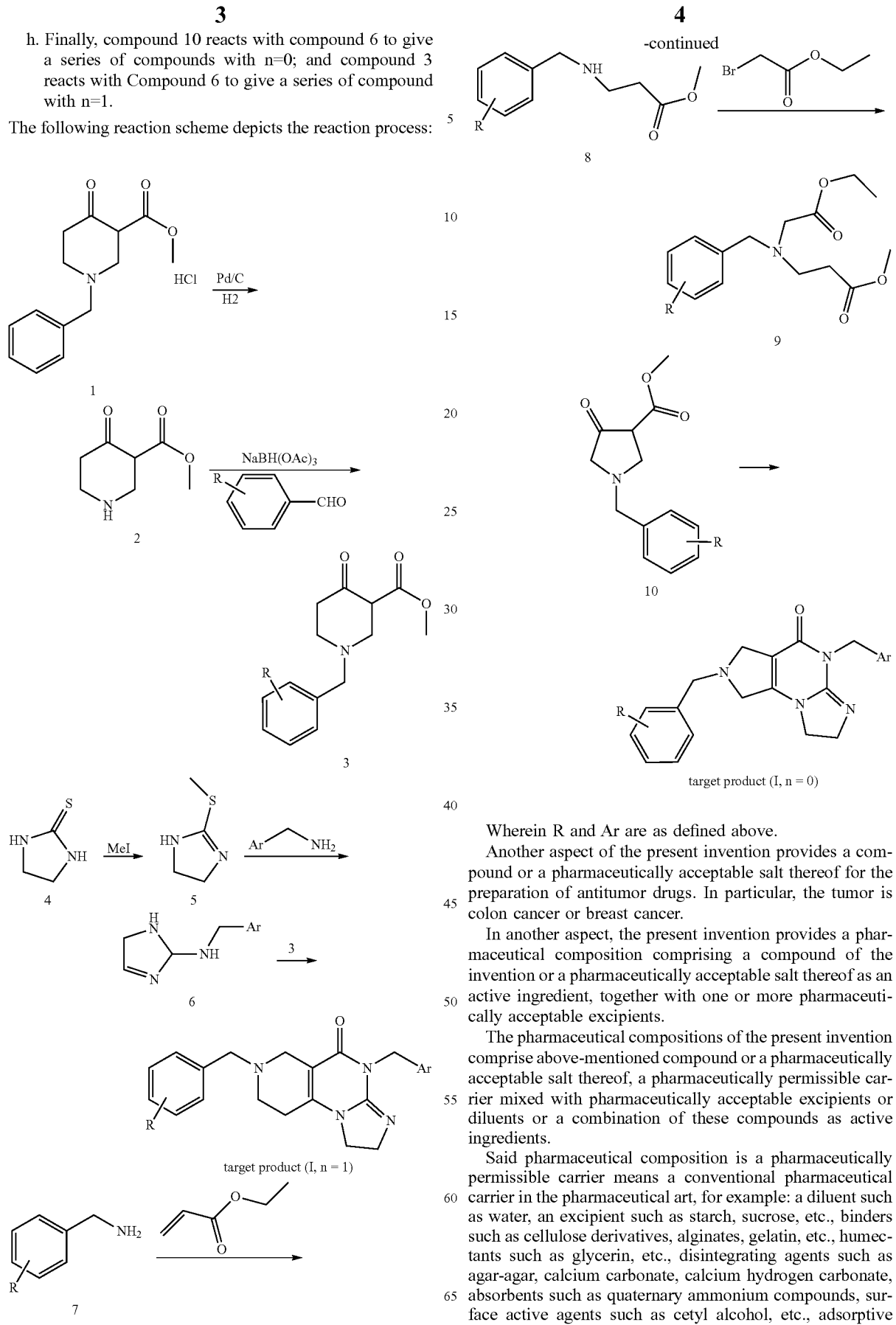

target product (I, n = 1)

target product (I, n = 0)

Wherein R and Ar are as defined above.

Another aspect of the present invention provides a compound or a pharmaceutically acceptable salt thereof for the preparation of antitumor drugs. In particular, the tumor is colon cancer or breast cancer.

In another aspect, the present invention provides a pharmaceutical composition comprising a compound of the invention or a pharmaceutically acceptable salt thereof as an active ingredient, together with one or more pharmaceutically acceptable excipients.

The pharmaceutical compositions of the present invention comprise above-mentioned compound or a pharmaceutically acceptable salt thereof, a pharmaceutically permissible carrier mixed with pharmaceutically acceptable excipients or diluents or a combination of these compounds as active ingredients.

Said pharmaceutical composition is a pharmaceutically permissible carrier means a conventional pharmaceutical carrier in the pharmaceutical art, for example: a diluent such as water, an excipient such as starch, sucrose, etc., binders such as cellulose derivatives, alginates, gelatin, etc., humectants such as glycerin, etc., disintegrating agents such as agar-agar, calcium carbonate, calcium hydrogen carbonate, absorbents such as quaternary ammonium compounds, surface active agents such as cetyl alcohol, etc., adsorptive carriers such as kaolin and other lubricating agents such as talc, calcium stearate, magnesium stearate, and similar compound. Other adjuvants such as flavoring agents, sweeteners, etc. can also be added in the composition.

The pharmaceutical compositions of the present invention may be provided by oral, inhalation, rectal or parenteral administration mode administered to a patient in need of such treatment. For oral administration, it can be made of conventional solid preparations such as tablets, powders, granules, capsules, etc., into a liquid preparation such as water or oil suspensions, or other liquid preparations such as syrups, tinctures and the like; for parenteral, the drug can be made into a solution for injection, aqueous or oily suspensions and the like, preferably in the form of tablets, capsules and injections.

The pharmaceutical compositions of various dosage forms provided by the invention may be produced according to conventional methods for preparation of the pharmaceutical art, for example, the active ingredient is mixed with one or more carriers, and then formed into the desired dosage form.

The compounds of the present invention and their pharmaceutically acceptable salts can stimulate the body to produce tumor necrosis factor-related apoptosis-inducing ligand, thereby providing new options for treatment of related tumors.

EXAMPLE 1

Synthesis of Compound I-1

7-Benzyl-4-(3-chlorobenzyl)-1,2,6,7,8,9-hexahydroimidazo[1,2-a]pyrido[3,4-e]pyrimidin-5(4H)-one

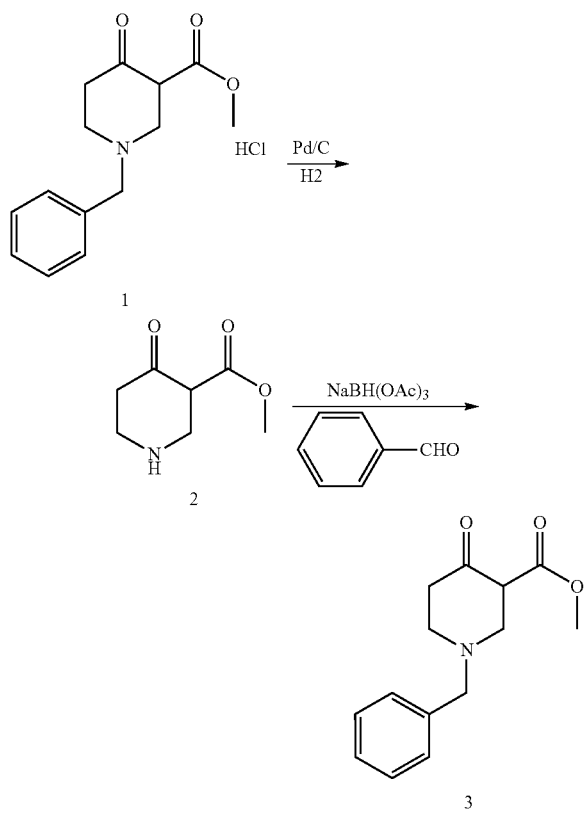

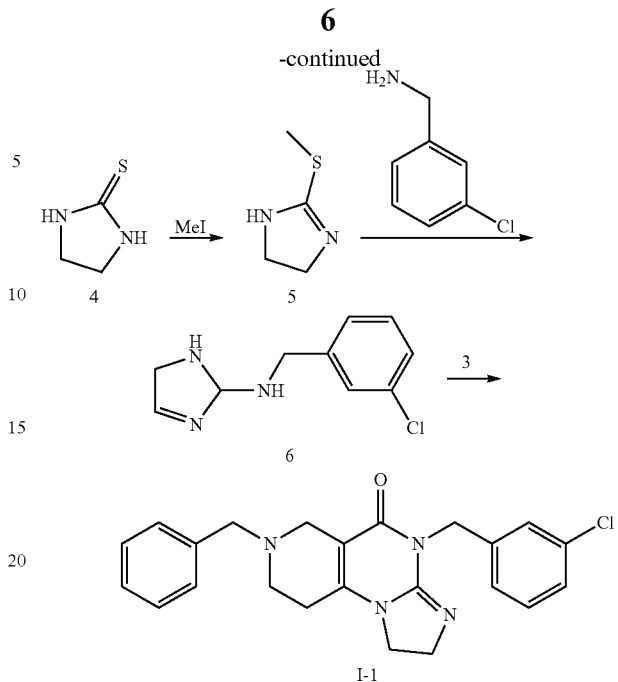

Step 1: Compound 1 (5 g, 17.7 mmol) and Pd/C (500 mg) was dissolved in methanol (25 mL). The mixture was hydrogenated for 12 hours at 30° C. LCMS confirmed the reaction was completed. The Pd/C was filtered off, and the filtrate was concentrated. Compound 2 was obtained (3.3 g, yield 96.5%). The product was used for next step without further purification.

Step 2: To a 50 mL three necked flask, was charged with compound 2 (1 g, 5.2 mmol), 1,2 dichlorethane (10 mL), DIEA (665 mg, 5.2 mmol). The mixture was stirred for 15 mixtures at 25° C. benzaldehyde (5.2 mmol) was added, followed by NaBH(OAc)$_3$ (6.7 mmol). The mixture was stirred for 2 hours at 25° C. LCMS confirmed that the reaction completed. The reaction was quenched with ice water (20 mL), extracted with dichloromethane 20 mL twice. The organic phase was combined and washed with saturated NaHCO$_3$ (25 mL), and concentrated. Compound 3 was obtained (1.22 g). The product was used for next step without further purification.

Step 3: Compound 4 (59.8 mmol) was dissolved in methanol (70 mL), CH$_3$I (89.7 mmol) was added dropwise at 25° C. After refluxed for 30 minutes, the solvent was removed under vacuum. The residue was stirred with MTBE (50 mL), and filtered. The solid was dried under vacuum to afford compound 5 (yield 83%) as white solid.

Step 4: Compound 5 (2 mmol), and (3-chlorophenyl) methanamine (4.2 mmol) was dissolved in dioxane (5 mL) and the solution was refluxed for 12 hours. LCMS confirmed that the reaction was completed. The solvent was removed, and the residue was stirred with toluene for 12 hours. The suspension was filtered and was dried under vacuum to afford compound 6

Step 5: A mixture of compound 3 (0.4 mmol), compound 6 (0.4 mmol), and MeONa (1.2 mmol) in methanol (3 mL) was refluxed for 15 hours. LCMS confirmed that the reaction was completed. The reaction was cooled down to room temperature. Half of the solvent was removed under vacuum. Water (2 mL) was added dropwise. Brown solid came out, filtered and washed with water. The solid was dried under vacuum to afford I-1 (yield 25%).

¹HNMR (CDCl₃), δ 2.44 (s, 2H), 2.65 (t, J=6.4 Hz, 2H), 3.29 (s, 2H), 3.65 (s, 2H), 3.87 (s, 4H), 5.01 (s, 2H), 7.19-7.42 (m, 9H); LC-MS: m/z=406.7(M+1).

EXAMPLE 2

Synthesis of Compound I-2

7-benzyl-4-(3-methylbenzyl)-1,2,6,7,8,9-hexahydroimidazo[1,2-a]pyrido[3,4-e]pyrimidin-5(4H)-one

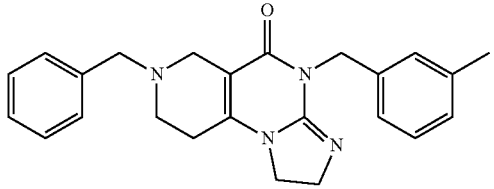
(I-2)

The procedure is same as Example 1 except:

in step 4, (3-chlorophenyl)methanamine is replaced by m-tolylmethanamine.

I-2 (yield: 22%), ¹HNMR (CDCl₃), δ 2.30 (s, 3H), 2.56 (s, 2H), 2.79 (s, 2H), 3.3-3.4(m, 4H), 3.76 (s, 2H), 3.97 (m, 4H), 5.05 (s, 2H), 7.04-7.32 (m, 9H); LC-MS: m/z=386.8(M+1).

EXAMPLE 3

Synthesis of Compound I-3

7-benzyl-4-(4-chlorobenzyl)-1,2,6,7,8,9-hexahydroimidazo[1,2-a]pyrido[3,4-e]pyrimidin-5(4H)-one

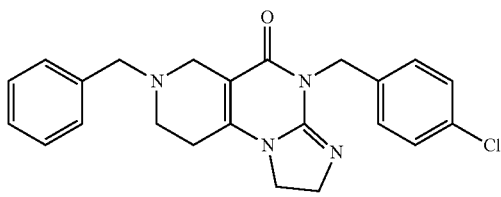
(I-3)

The procedure is same as Example 1 except:

in step 4, the (3-chlorophenyl)methanamine is replaced by (4-chlorophenyl)methanamine.

I-3 (yield: 30%), ¹HNMR (CDCl₃), δ 2.50 (s, 2H), 2.62 (t, J=6.4 Hz, 2H), 3.01 (s, 2H), 3.60 (s, 2H), 3.70 (t, J=8.8 Hz, 3H), 3.93(t, J=8.8 Hz, 2H), 4.87 (s, 2H), 7.21-7.38 (m, 9H); LC-MS: m/z=406.7(M+1).

EXAMPLE 4

Synthesis of Compound I-4

7-benzyl-4-(2-(trifluoromethyl)benzyl)-1,2,6,7,8,9-hexahydroimidazo[1,2-a]pyrido[3,4-e]pyrimidin-5(4H)-one

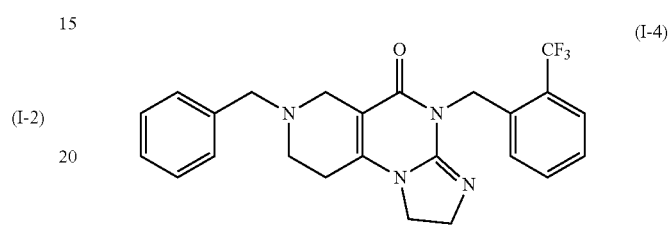
(I-4)

The procedure is same as Example 1 except:

in step 4, (3-chlorophenyl)methanamine is replaced by (2-(trifluoromethyl)phenyl)methanamine.

I-4 (yield: 25%), ¹HNMR (CDCl₃), δ 2.54 (s, 2H), 2.71 (s, 2H), 3.32 (s, 2H), 3.68 (s, 2H), 3.85-3.97 (m, 4H), 5.30 (s, 2H), 7.10 (d, J=7.6 Hz, 1H), 7.28-7.33 (m, 6H), 7.43 (t, J=7.6 Hz, 1H), 7.63 (d, J=7.6 Hz, 1H); LC-MS: m/z=440.7 (M+1).

EXAMPLE 5

Synthesis of Compound I-5

7-benzyl-4-(2-bromobenzyl)-1,2,6,7,8,9-hexahydroimidazo[1,2-a]pyrido[3,4-e]pyrimidin-5(4H)-one

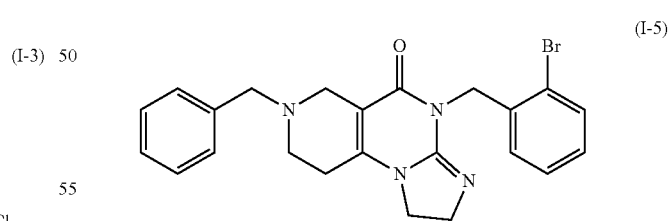
(I-5)

The procedure is same as Example 1 except:

in step 4, (3-chlorophenyl)methanamine is replaced by (2-bromophenyl)methanamine I-5 (yield: 30%), ¹HNMR (CDCl₃), δ 2.49 (t, J=5.6 Hz, 2H), 2.67 (t, J=5.6 Hz, 2H), 3.31 (s, 2H), 3.66 (s, 2H), 3.81-3.91 (m, 4H), 5.11 (s, 2H), 6.97 (d, J=8.0 Hz, 1H), 7.03 (t, J=6.4 Hz, 1H), 7.19 (t, J=7.2 Hz, 1H), 7.24-7.32 (m, 5H), 7.51 (d, J=8.0 Hz, 1H); LC-MS: m/z=450.6, 452.6(M+1).

EXAMPLE 6

Synthesis of Compound I-6

4-(2-methylbenzyl)-7-(4-(trifluoromethyl)benzyl)-1,2,6,7,8,9-hexahydroimidazo[1,2-a]pyrido[3,4-e]pyrimidin-5(4H)-one

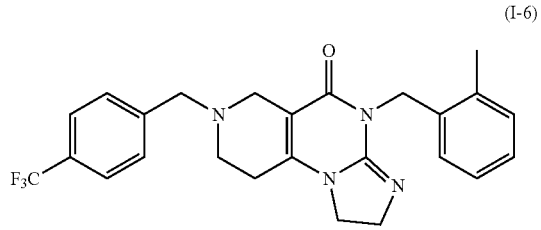 [SMILES: Cc1ccccc1CN1C(=O)C2=C(CCN(Cc3ccc(C(F)(F)F)cc3)C2)N2CCN=C12]

(I-6)

The procedure is same as Example 1 except:

In step 2: benzaldehyde is replaced by 4-(trifluoromethyl)benzaldehyde

In step 4: (3-chlorophenyl)methanamine is replaced by o-tolylmethanamine

I-6 (yield 26%), ¹HNMR (CD$_3$OD), δ 2.38 (s, 3H), 2.68 (t, J=5.6 Hz, 2H), 2.81 (t, J=5.6 Hz, 2H), 3.26 (s, 2H), 3.85 (m, 4H), 4.09 (t, J=5.2 Hz, 2H), 5.02 (s, 2H), 6.89 (d, J=7.2 Hz, 2H), 7.0-7.3 (m, 3H), 7.59 (d, J=8.0 Hz, 2H), 7.66 (d, J=8.0 Hz, 2H); LC-MS: m/z=455.2(M+1).

EXAMPLE 7

Synthesis of Compound I-7

7-(4-methoxybenzyl)-4-(2-methylbenzyl)-1,2,6,7,8,9-hexahydroimidazo[1,2-a]pyrido[3,4-e]pyrimidin-5(4H)-one

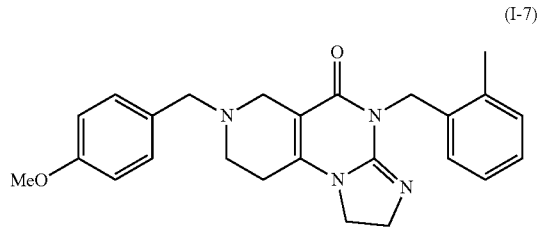 [SMILES: COc1ccc(CN2CCC3=C(C2)C(=O)N(Cc2ccccc2C)C2=NCCN23)cc1]

(I-7)

The procedure is same as Example 1 except:

In step 2: benzaldehyde is replaced by 4-methoxybenzaldehyde

In step 4: (3-chlorophenyl)methanamine is replaced by o-tolylmethanamine

I-7 (yield 30%), ¹HNMR (CD$_3$OD), δ 2.38 (s, 3H), 2.70 (d, J=5.3 Hz, 2H), 2.78 (d, J=5.3 Hz, 2H), 3.23 (s, 2H), 3.66 (s, 2H), 3.80 (s, 3H), 3.84 (t, J=8.4 Hz, 2H), 4.07 (t, J=8.4 Hz, 2H), 5.01 (s, 2H), 6.87-6.92 (m, 3H), 7.08-7.18 (m, 3H), 7.29 (t, J=8.8 Hz, 2H); LC-MS: m/z=417.2(M+1).

EXAMPLE 8

Synthesis of Compound I-8

4-(2-methylbenzyl)-7-(4-morpholinobenzyl)-1,2,6,7,8,9-hexahydroimidazo[1,2-a]pyrido[3,4-e]pyrimidin-5(4H)-one

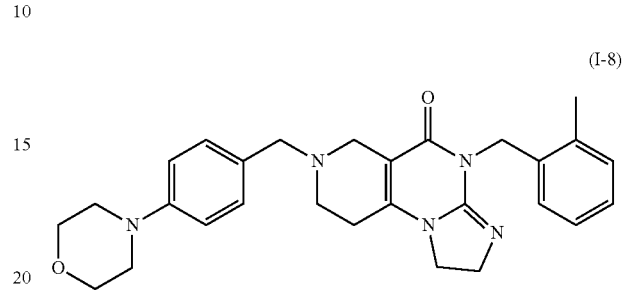

(I-8)

The procedure is same as Example 1 except:

In step 2: benzaldehyde is replaced by 4-morpholinobenzaldehyde

In step 4: (3-chlorophenyl)methanamine is replaced by o-tolylmethanamine

I-8 (yield 20%), ¹HNMR (CD$_3$OD), δ 2.37 (s, 3H), 2.61 (t, J=5.6 Hz, 2H), 2.75 (t, J=5.6 Hz, 2H), 3.13 (t, J=4.8 Hz, 4H), 3.22 (s, 2H), 3.63 (s, 2H), 3.72-3.84 (m, 6H), 4.04 (t, J=8.8 Hz, 2H), 5.00 (s, 2H), 6.88 (d, J=7.6 Hz, 1H), 6.95 (d, J=8.4 Hz, 2H), 7.07-7.17 (m, 3H), 7.27 (d, J=8.4 Hz, 2H); LC-MS: m/z=472.2(M+1).

EXAMPLE 9

Synthesis of Compound I-9

4-(2-methylbenzyl)-7-(3-(trifluoromethyl)benzyl)-1,2,6,7,8,9-hexahydroimidazo[1,2-a]pyrido[3,4-e]pyrimidin-5(4H)-one

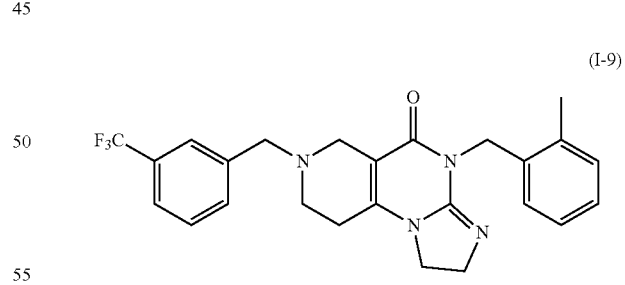

(I-9)

The procedure is same as Example 1 except:

In step 2: benzaldehyde is replaced by 3-(trifluoromethyl)benzaldehyde

In step 4: (3-chlorophenyl)methanamine is replaced by o-tolylmethanamine

I-9 (yield 25%), ¹HNMR (CD$_3$OD), δ 2.38 (s, 3H), 2.68 (d, J=5.6 Hz, 2H), 2.81 (t, J=5.6 Hz, 2H), 3.26 (s, 2H), 3.80 (s, 2H), 3.84 (t, J=8.8 Hz, 2H), 4.09 (t, J=8.8 Hz, 2H), 5.02 (s, 2H), 6.89 (d, J=7.2 Hz, 1H), 7.09-7.24 (m, 3H), 7.56-7.72 (m, 4H); LC-MS: m/z=455.2(M+1).

EXAMPLE 10

Synthesis of Compound I-10

4-(2-methylbenzyl)-7-(4-(4-methylpiperazin-1-yl)benzyl)-1,2,6,7,8,9-hexahydroimidazo[1,2-a]pyrido[3,4-e]pyrimidin-5(4H)-one

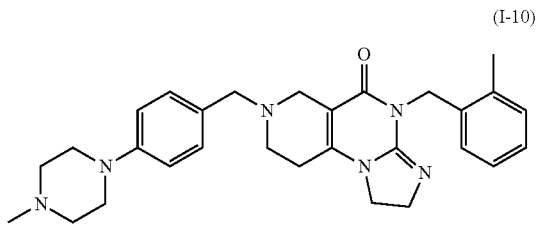 [SMILES: Cc1ccccc1CN1C(=O)C2=C(CCN(Cc3ccc(N4CCN(C)CC4)cc3)C2)N2CCN=C12]
(I-10)

The procedure is same as Example 1 except:

In step 2: benzaldehyde is replaced by 4-(4-methylpiperazin-1-yl)benzaldehyde

In step 4: (3-chlorophenyl)methanamine is replaced by o-tolylmethanamine

I-10 (yield 19%), $^1$HNMR (CD$_3$OD), δ 2.35-2.38 (m, 6H), 2.61 (s, 6H), 2.75 (t, J=5.6 Hz, 2H), 3.21 (m, 6H), 3.63 (s, 2H), 3.81 (t, J=8.8 Hz, 2H), 4.04 (t, J=8.8 Hz, 2H), 5.01 (s, 2H), 6.88 (d, J=7.2 Hz, 1H), 6.96 (d, J=7.2 Hz, 2H), 7.05-7.17 (m, 3H), 7.26 (d, J=8.4 Hz, 2H); LC-MS: m/z=485.3(M+1).

EXAMPLE 11

Synthesis of Compound I-11

4,7-bis(2-fluorobenzyl)-1,2,6,7,8,9-hexahydroimidazo[1,2-a]pyrido[3,4-e]pyrimidin-5(4H)-one

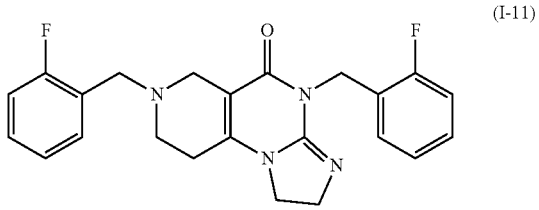
(I-11)

The procedure is same as Example 1 except:

In step 2: benzaldehyde is replaced by 2-fluorobenzaldehyde

In step 4: (3-chlorophenyl)methanamine is replaced by (2-fluorophenyl)methanamine I-11 (yield 25%), $^1$HNMR (CD$_3$OD), δ 2.58 (t, J=5.6 Hz, 3H), 2.77 (t, J=5.6 Hz, 2H), 3.26 (s, 2H), 3.6-3.9 (m, 4H), 3.94-3.99 (m, 2H), 5.09 (s, 2H), 7.04-7.17 (m, 6H), 7.21-7.28 (m, 2H), 7.4-7.5(m, 2H); LC-MS: m/z=409.2(M+1).

EXAMPLE 12

Synthesis of Compound I-12

7-(2-fluorobenzyl)-4-(2-(trifluoromethyl)benzyl)-1,2,6,7,8,9-hexahydroimidazo[1,2-a]pyrido[3,4-e]pyrimidin-5(4H)-one

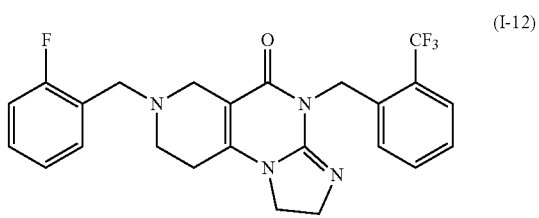
(I-12)

The procedure is same as Example 1 except:

In step 2: benzaldehyde is replaced by 2-fluorobenzaldehyde

In step 4: (3-chlorophenyl)methanamine is replaced by (2-(trifluoromethyl)phenyl)methanamine I-12 (yield 26%), $^1$HNMR (DMSO_d6), δ 2.59 (s, 2H), 2.70 (t, J=5.6 Hz, 2H), 3.67 (t, J=9.2 Hz, 2H), 3.69 (s, 2H), 3.98 (t, J=9.2 Hz, 2H), 5.10 (s, 2H), 7.07 (d, J=8.0 Hz, 1H), 7.15-7.25 (m, 2H), 7.3-7.4 (m, 1H), 7.40-7.50 (m, 2H), 7.59 (t, J=7.6 Hz, 1H), 7.73 (d, J=7.6 Hz, 1H); LC-MS: m/z=459.2(M+1).

EXAMPLE 13

Synthesis of Compound I-13

4-(2-chlorobenzyl)-7-(2-fluorobenzyl)-1,2,6,7,8,9-hexahydroimidazo[1,2-a]pyrido[3,4-e]pyrimidin-5(4H)-one

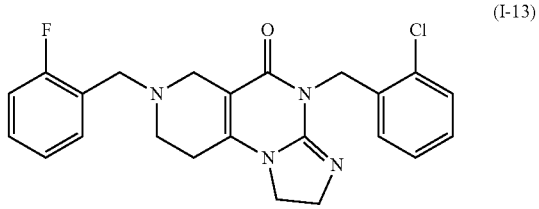
(I-13)

The procedure is same as Example 1 except:

In step 2: benzaldehyde is replaced by 2-fluorobenzaldehyde

In step 4: (3-chlorophenyl)methanamine is replaced by (2-chlorophenyl)methanamine I-13 (yield 30%), $^1$HNMR (DMSO_d6), δ 2.58 (d, J=5.6 Hz, 2H), 2.69 (t, J=5.6 Hz, 2H), 3.07 (s, 2H), 3.59 (s, 2H), 3.67 (t, J=9.2 Hz, 2H), 3.98 (t, J=9.2 Hz, 2H), 4.96 (s, 2H), 6.94-6.96 (m, 1H), 7.15 (m, 3H), 7.24-7.28 (m, 2H), 7.41-7.46 (m, 2H); LC-MS: m/z=425.1(M+1).

EXAMPLE 14

Synthesis of Compound I-14

4-(2-bromobenzyl)-7-(2-fluorobenzyl)-1,2,6,7,8,9-hexahydroimidazo[1,2-a]pyrido[3,4-e]pyrimidin-5(4H)-one

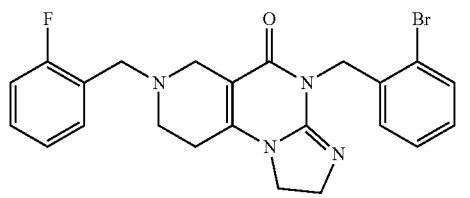

(I-14)

The procedure is same as Example 1 except:

In step 2: benzaldehyde is replaced by 2-fluorobenzaldehyde

In step 4: (3-chlorophenyl)methanamine is replaced by (2-bromophenyl)methanamine I-14 (yield 35%), $^1$HNMR (CD$_3$OD), δ 2.58 (s, 2H), 2.68 (t, J=5.6 Hz, 2H), 3.09 (s, 2H), 3.64-3.69 (m, 4H), 3.98 (t, J=8.8 Hz, 2H), 4.90 (s, 2H), 6.90 (d, J=7.6 Hz, 1H), 7.10-7.20 (m, 3H), 7.28-7.36 (m, 2H), 7.43 (t, J=7.2 Hz, 1H), 7.61 (d, J=7.6 Hz, 1H); LC-MS: m/z=468.2, 470.2(M+1).

EXAMPLE 15

Synthesis of Compound I-15

7-(2-fluorobenzyl)-4-(2-methylbenzyl)-1,2,6,7,8,9-hexahydroimidazo[1,2-a]pyrido[3,4-e]pyrimidin-5(4H)-one

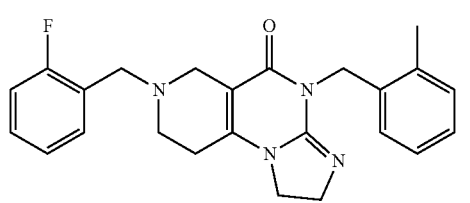

(I-15)

The procedure is same as Example 1 except:

In step 2: benzaldehyde is replaced by 2-fluorobenzaldehyde

In step 4: (3-chlorophenyl)methanamine is replaced by o-tolylmethanamine

I-15 (yield 20%), $^1$HNMR (CD$_3$OD), δ 2.34 (s, 3H), 2.64 (t, J=5.6 Hz, 2H), 2.77 (t, J=5.6 Hz, 2H), 3.24 (s, 2H), 3.72 (s, 2H), 3.82 (t, J=4.8 Hz, 2H), 4.6 (t, J=4.8 Hz, 2H), 5.00 (s, 2H), 6.89 (d, J=7.2 Hz, 1H), 7.00-7.24 (m, 6H), 7.33-7.38 (m, 1H); LC-MS: m/z=405.5(M+1).

EXAMPLE 16

Synthesis of Compound I-16

7-(2-bromobenzyl)-4-(2-fluorobenzyl)-1,2,6,7,8,9-hexahydroimidazo[1,2-a]pyrido[3,4-e]pyrimidin-5(4H)-one

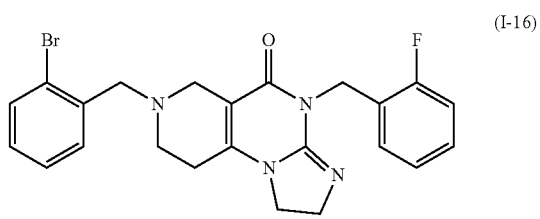

(I-16)

The procedure is same as Example 1 except:

In step 2: benzaldehyde is replaced by 2-bromobenzaldehyde

In step 4: (3-chlorophenyl)methanamine is replaced by (2-fluorophenyl)methanamine I-16 (yield 30%). $^1$HNMR (CD$_3$OD), δ 2.61 (s, 2H), 2.80 (t, J=5.2 Hz, 2H), 3.29 (s, 2H), 3.80 (s, 1H), 3.83 (t, J=8.8 Hz, 4H), 4.03 (t, J=8.8 Hz, 2H), 5.10 (s, 2H), 7.05-7.20 (m, 4H), 7.25 (t, J=6.4 Hz, 2H), 7.51 (d, J=7.2 Hz, 1H), 7.59 (d, J=7.2 Hz, 1H); LC-MS: m/z=469.14, 470.14(M+1).

EXAMPLE 17

Synthesis of Compound I-17

7-(2-bromobenzyl)-4-(2-(trifluoromethyl)benzyl)-1,2,6,7,8,9-hexahydroimidazo[1,2-a]pyrido[3,4-e]pyrimidin-5(4H)-one

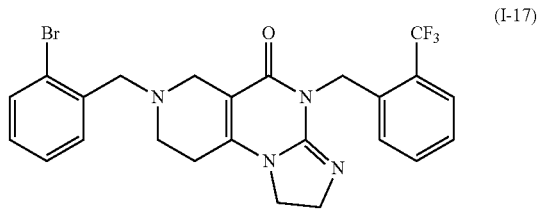

(I-17)

The procedure is same as Example 1 except:

In step 2: benzaldehyde is replaced by 2-bromobenzaldehyde

In step 4: (3-chlorophenyl)methanamine is replaced by (2-(trifluoromethyl)phenyl)methanamine I-17 (yield 30%), $^1$HNMR (DMSO_d6), δ 2.61 (s, 2H), 2.74 (t, J=5.2 Hz, 2H), 3.16 (m, 2H), 3.66-3.72 (m, 4H), 4.01 (t, J=8.8 Hz, 2H), 5.11 (s, 2H), 7.09 (d, J=7.6 Hz, 1H), 7.22 (t, J=7.6 Hz, 1H), 7.39 (t, J=6.8 Hz, 1H), 7.48 (t, J=8.8 Hz, 2H), 7.61 (t, J=7.6 Hz, 2H), 7.74 (d, J=8 Hz, 1H); LC-MS: m/z=519.1(M+1).

EXAMPLE 18

Synthesis of Compound I-18

7-(2-bromobenzyl)-4-(2-chlorobenzyl)-1,2,6,7,8,9-hexahydroimidazo[1,2-a]pyrido[3,4-e]pyrimidin-5(4H)-one

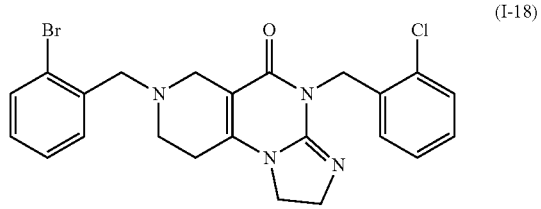
(I-18)

The procedure is same as Example 1 except:

In step 2: benzaldehyde is replaced by 2-bromobenzaldehyde

In step 4: (3-chlorophenyl)methanamine is replaced by (2-chlorophenyl)methanamine I-18 (yield 35%), $^1$HNMR (DMSO_d6), δ 2.60 (t, J=5.6 Hz, 2H), 2.73 (t, J=5.6 Hz, 2H), 3.2(d, J=8.8 Hz, 2H), 3.65-3.71 (m, 4H), 4.00 (t, J=5.2 Hz, 2H), 4.96 (s, 2H), 6.96 (t, J=3.6 Hz, 1H), 7.20-7.29 (m, 3H), 7.39 (t, J=7.2 Hz, 1H), 7.44-7.50 (m, 2H), 7.62 (d, J=7.6 Hz, 1H); LC-MS: m/z=487.1(M+1).

EXAMPLE 19

Synthesis of Compound I-19

4,7-bis(2-bromobenzyl)-1,2,6,7,8,9-hexahydroimidazo[1,2-a]pyrido[3,4-e]pyrimidin-5(4H)-one

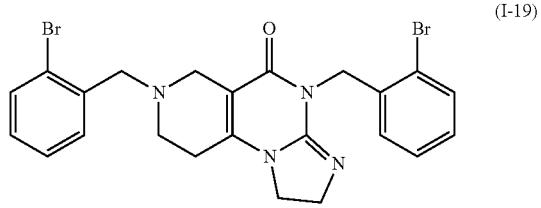 [SMILES: O=C1C2=C(CCN(Cc3ccccc3Br)C2)N2CCN=C2N1Cc1ccccc1Br]
(I-19)

The procedure is same as Example 1 except:

In step 2: benzaldehyde is replaced by 2-bromobenzaldehyde

In step 4: (3-chlorophenyl)methanamine is replaced by (2-bromophenyl)methanamine I-19 (yield 40%), $^1$HNMR (DMSO_d6), δ 2.50 (s, 2H), 2.73 (s, 2H), 3.14 (s, 2H), 3.60-3.71 (m, 4H), 3.99 (s, 2H), 4.91 (s, 2H), 6.91 (d, J=5.2 Hz, 1H), 7.22-7.49 (m, 5H), 7.61 (s, 2H); LC-MS: m/z=531.1(M+1).

EXAMPLE 20

Synthesis of Compound I-20

7-(2-bromobenzyl)-4-(2-methylbenzyl)-1,2,6,7,8,9-hexahydroimidazo[1,2-a]pyrido[3,4-e]pyrimidin-5(4H)-one

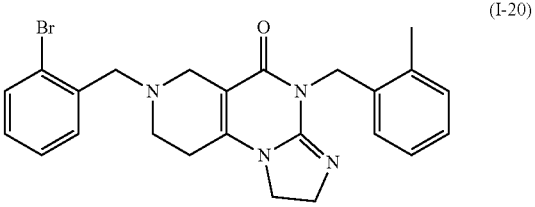 [SMILES: Cc1ccccc1CN1C(=O)C2=C(CCN(Cc3ccccc3Br)C2)N2CCN=C12]
(I-20)

The procedure is same as Example 1 except:

In step 2: benzaldehyde is replaced by 2-bromobenzaldehyde

In step 4: (3-chlorophenyl)methanamine is replaced by o-tolylmethanamine

I-20 (yield 30%), $^1$HNMR(CD$_3$OD), δ 2.38 (s, 3H), 2.61 (s, 2H), 2.81 (t, J=5.2 Hz, 2H), 3.32 (m, 2H), 3.78-3.83 (m, 4H), 4.02 (t, J=9.2 Hz, 2H), 5.00 (s, 2H), 6.90 (d, J=6.8 Hz, 1H), 7.05-7.20 (m, 4H), 7.34 (t, J=6.8 Hz, 1H), 7.51 (d, J=7.6 Hz, 1H), 7.59 (d, J=8.0 Hz, 1H); LC-MS: m/z=465.1 (M+1).

EXAMPLE 21

Synthesis of Compound I-21

4-(2-fluorobenzyl)-7-(2-methylbenzyl)-1,2,6,7,8,9-hexahydroimidazo[1,2-a]pyrido[3,4-e]pyrimidin-5(4H)-one

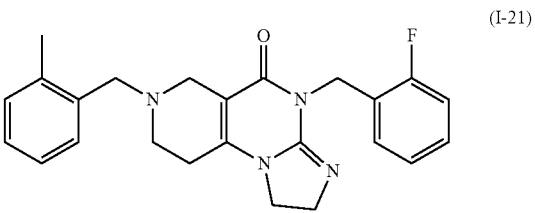 [SMILES: Cc1ccccc1CN1CCC2=C(C1)C(=O)N(Cc1ccccc1F)C1=NCCN12]
(I-21)

The procedure is same as Example 1 except:

In step 2: benzaldehyde is replaced by 2-methylbenzaldehyde

In step 4: (3-chlorophenyl)methanamine is replaced by (2-fluorophenyl)methanamine I-21 (yield 20%), $^1$HNMR(CD$_3$OD), δ 2.38 (s, 3H), 2.53 (t, J=5.6 Hz, 2H), 2.73 (t, J=5.6 Hz, 2H), 3.22 (s, 2H), 3.81 (m, 2H), 3.97 (m, 2H), 5.09 (s, 2H), 7.05-7.17 (m, 6H), 7.21-7.28 (m, 2H); LC-MS: m/z=405.5(M+1).

EXAMPLE 22

Synthesis of Compound I-22

7-(2-methylbenzyl)-4-(2-(trifluoromethyl)benzyl)-1,2,6,7,8,9-hexahydroimidazo[1,2-a]pyrido[3,4-e]pyrimidin-5(4H)-one

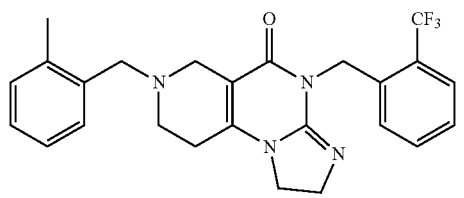
(I-22)

The procedure is same as Example 1 except:

In step 2: benzaldehyde is replaced by 2-methylbenzaldehyde

In step 4: (3-chlorophenyl)methanamine is replaced by (2-(trifluoromethyl)phenyl)methanamine I-22 (yield 21%), $^1$HNMR (DMSO_d6), δ 2.32 (s, 3H), 2.57 (s, 2H), 2.68 (t, J=5.2 Hz, 2H), 3.06 (s, 2H), 3.59 (s, 2H), 3.67 (t, J=9.2 Hz, 2H), 3.99 (t, J=9.2 Hz, 2H), 5.10 (s, 2H), 7.07 (d, J=8.0 Hz, 1H), 7.16-7.21(m, 3H), 7.26 (d, J=6.0 Hz, 1H), 7.45 (t, J=7.6 Hz, 1H), 7.60 (t, J=7.6 Hz, 1H), 7.73 (d, J=7.6 Hz, 1H); LC-MS: m/z=455.2(M+1).

EXAMPLE 23

Synthesis of Compound I-23

7-(2-chlorobenzyl)-4-(2-fluorobenzyl)-1,2,6,7,8,9-hexahydroimidazo[1,2-a]pyrido[3,4-e]pyrimidin-5(4H)-one

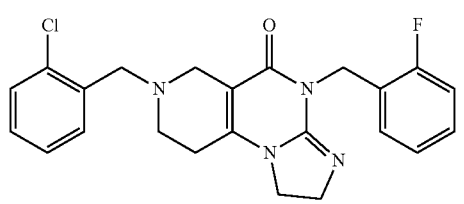
(I-23)

The procedure is same as Example 1 except:

In step 2: benzaldehyde is replaced by 2-chlorobenzaldehyde

In step 4: (3-chlorophenyl)methanamine is replaced by (2-fluorophenyl)methanamine I-23 (yield 22%), $^1$HNMR(CD$_3$OD), δ 2.61 (s, 2H), 2.80 (t, J=4.8 Hz, 2H), 3.31 (s, 2H), 3.81 (m, 4H), 4.03 (t, J=8.8 Hz, 2H), 5.10 (s, 2H), 7.05-7.14 (m, 3H), 7.25-7.32 (m, 3H), 7.40 (d, J=7.2 Hz, 1H), 7.51 (d, J=7.2 Hz, 1H); LC-MS: m/z=425.1(M+1).

EXAMPLE 24

Synthesis of Compound I-24

7-(2-chlorobenzyl)-4-(2-(trifluoromethyl)benzyl)-1,2,6,7,8,9-hexahydroimidazo[1,2-a]pyrido[3,4-e]pyrimidin-5(4H)-one

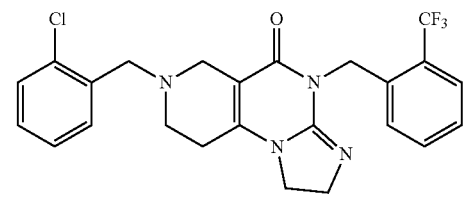
(I-24)

The procedure is same as Example 1 except:

In step 2: benzaldehyde is replaced by 2-chlorobenzaldehyde

In step 4: (3-chlorophenyl)methanamine is replaced by (2-(trifluoromethyl)phenyl)methanamine I-24 (yield 25%), $^1$HNMR (DMSO_d6), δ 2.60 (s, 2H), 2.74 (t, J=5.6 Hz, 2H), 3.13 (s, 2H), 3.67 (t, J=9.2 Hz, 2H), 3.73 (s, 2H), 4.00 (t, J=5.2 Hz, 2H), 5.10 (s, 2H), 7.08 (d, J=8.0 Hz, 1H), 7.29-7.36 (m, 2H), 7.44-7.51 (m, 3H), 7.60 (t, J=7.6 Hz, 1H), 7.73 (t, J=7.6 Hz, 1H); LC-MS: m/z=475.1 (M+1).

EXAMPLE 25

Synthesis of Compound I-25

4,7-bis(2-chlorobenzyl)-1,2,6,7,8,9-hexahydroimidazo[1,2-a]pyrido[3,4-e]pyrimidin-5(4H)-one

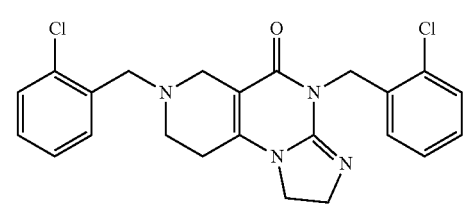
(I-25)

The procedure is same as Example 1 except:

In step 2: benzaldehyde is replaced by 2-chlorobenzaldehyde

In step 4: (3-chlorophenyl)methanamine is replaced by (2-chlorophenyl)methanamine I-25 (yield 28%), $^1$HNMR (DMSO_d6), δ 2.59 (s, 2H), 2.72 (s, 2H), 3.13 (s, 2H), 3.65-3.73 (m, 4H), 3.99 (t, J=8.4 Hz, 2H), 4.96 (s, 2H), 6.96 (s, 1H), 7.27-7.34 (m, 4H), 7.44-7.51 (m, 3H); LC-MS: m/z=441.1(M+1).

EXAMPLE 26

Synthesis of Compound I-26

4-(2-bromobenzyl)-7-(2-chlorobenzyl)-1,2,6,7,8,9-hexahydroimidazo[1,2-a]pyrido[3,4-e]pyrimidin-5(4H)-one

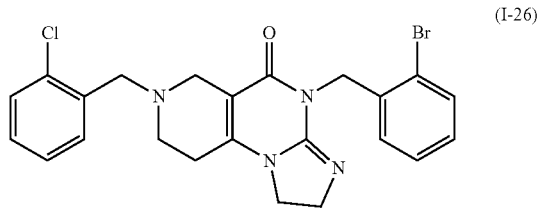 [SMILES: O=C1C2=C(CCN(Cc3ccccc3Cl)C2)N2CCN=C2N1Cc1ccccc1Cl]
(I-26)

The procedure is same as Example 1 except:

In step 2: benzaldehyde is replaced by 2-chlorobenzaldehyde

In step 4: (3-chlorophenyl)methanamine is replaced by (2-bromophenyl)methanamine I-26 (yield 28%), ¹HNMR (DMSO_d6), δ 2.59 (s, 2H), 2.73 (t, J=5.6 Hz, 2H), 3.13 (s, 2H), 3.67 (t, J=8.8 Hz, 2H), 3.74 (s, 2H), 3.99 (t, J=8.8 Hz, 2H), 4.91 (s, 2H), 6.91 (d, J=7.6 Hz, 1H), 7.19 (t, J=6.8 Hz, 1H), 7.30-7.36 (m, 3H), 7.43-7.51(m, 2H), 7.62 (d, J=8.0 Hz, 1H); LC-MS: m/z=487.1(M+1).

EXAMPLE 27

Synthesis of Compound I-27

7-(2-chlorobenzyl)-4-(2-methylbenzyl)-1,2,6,7,8,9-hexahydroimidazo[1,2-a]pyrido[3,4-e]pyrimidin-5(4H)-one

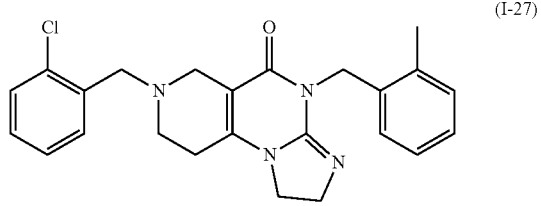 [SMILES: Cc1ccccc1CN1C(=O)C2=C(CCN(Cc3ccccc3Cl)C2)N2CCN=C12]
(I-27)

The procedure is same as Example 1 except:

In step 2: benzaldehyde is replaced by 2-chlorobenzaldehyde

In step 4: (3-chlorophenyl)methanamine is replaced by o-tolylmethanamine

I-27 (yield 25%), ¹HNMR(CD₃OD), δ 2.38 (s, 3H), 2.59 (s, 2H), 2.79 (t, J=5.2 Hz, 2H), 3.30 (s, 2H), 3.79 (m, 4H), 4.00 (t, J=8.8 Hz, 2H), 5.00 (s, 2H), 6.90 (d, J=5.2 Hz, 1H), 7.05-7.16 (m, 3H), 7.24-7.32 (m, 2H), 7.40 (d, J=6.8 Hz, 1H), 7.51 (d, J=6.8 Hz, 1H); LC-MS: m/z=421.1(M+1).

EXAMPLE 28

Synthesis of Compound I-28

7-(3-bromobenzyl)-4-(2-chlorobenzyl)-1,2,6,7,8,9-hexahydroimidazo[1,2-a]pyrido[3,4-e]pyrimidin-5(4H)-one

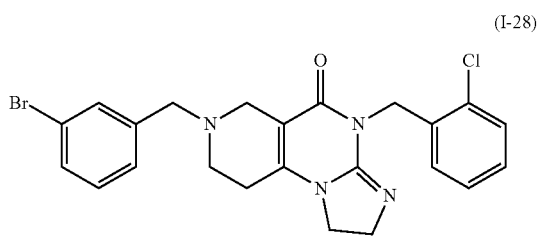 [SMILES: O=C1C2=C(CCN(Cc3cccc(Br)c3)C2)N2CCN=C2N1Cc1ccccc1Cl]
(I-28)

The procedure is same as Example 1 except:

In step 2: benzaldehyde is replaced by 3-bromobenzaldehyde

In step 4: (3-chlorophenyl)methanamine is replaced by (2-chlorophenyl)methanamine I-28 (yield 30%,), NMR (DMSO_d6), δ 2.58 (s, 2H), 2.65 (d, J=4.8 Hz, 2H), 3.06 (s, 2H), 3.67 (m, 4H), 3.98 (t, J=8.8 Hz, 2H), 4.96 (s, 2H), 6.95 (t, J=4.8 Hz, 1H), 7.26-7.33 (m, 4H), 7.44-7.53 (m, 3H); LC-MS: m/z=487.1(M+1).

EXAMPLE 29

Synthesis of Compound I-29

7-(3-bromobenzyl)-4-(2-methylbenzyl)-1,2,6,7,8,9-hexahydroimidazo[1,2-a]pyrido[3,4-e]pyrimidin-5(4H)-one

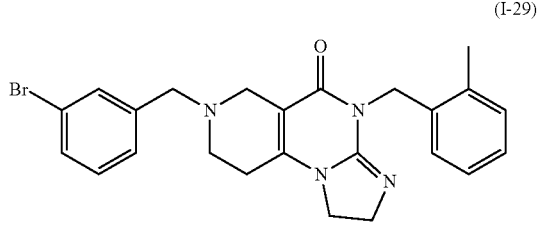 [SMILES: Cc1ccccc1CN1C(=O)C2=C(CCN(Cc3cccc(Br)c3)C2)N2CCN=C12]
(I-29)

The procedure is same as Example 1 except:

In step 2: benzaldehyde is replaced by 3-bromobenzaldehyde

In step 4: (3-chlorophenyl)methanamine is replaced by o-tolylmethanamine

I-29 (yield 38%), ¹HNMR (DMSO_d6), δ 2.32 (s, 3H), 2.57 (t, J=4.8 Hz, 2H), 2.65 (t, J=4.8 Hz, 2H), 3.06 (s, 2H), 3.63 (s, 2H), 3.68 (t, J=8.8 Hz, 2H), 3.97 (t, J=8.8 Hz, 2H), 4.87 (s, 2H), 6.89 (d, J=6.4 Hz, 1H), 7.08-7.14 (m, 3H), 7.30-7.35 (m, 2H), 7.46 (d, J=7.6 Hz, 1H), 7.53 (s, 1H); LC-MS: m/z=465.1(M+1).

EXAMPLE 30

Synthesis of Compound I-30

4-(2-fluorobenzyl)-7-(3-methylbenzyl)-1,2,6,7,8,9-hexahydroimidazo[1,2-a]pyrido[3,4-e]pyrimidin-5(4H)-one

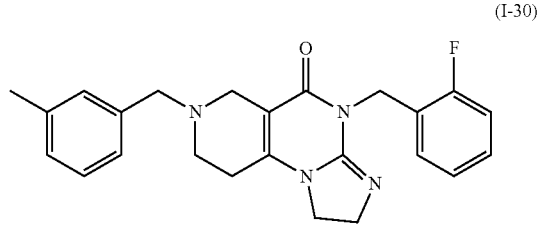
(I-30)

The procedure is same as Example 1 except:

In step 2: benzaldehyde is replaced by 3-methylbenzaldehyde

In step 4: (3-chlorophenyl)methanamine is replaced by (2-fluorophenyl)methanamine I-30 (yield 25%), $^1$HNMR(CD$_3$OD) δ 2.34 (s, 3H), 2.58 (s, 2H), 2.72 (t, J=5.2 Hz, 2H), 3.21 (s, 2H), 3.65 (s, 2H), 3.81 (t, J=9.2 Hz, 2H), 4.00 (t, J=9.2 Hz, 2H), 5.10 (s, 2H), 7.04-7.26 (m, 8H); LC-MS: m/z=405.2(M+1).

EXAMPLE 31

Synthesis of Compound I-31

7-(3-methylbenzyl)-4-(2-(trifluoromethyl)benzyl)-1,2,6,7,8,9-hexahydroimidazo[1,2-a]pyrido[3,4-e]pyrimidin-5(4H)-one

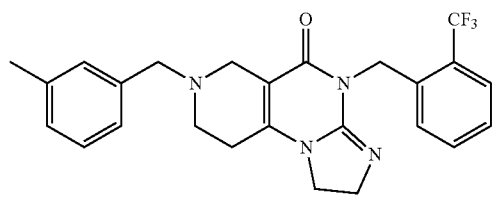
(I-31)

The procedure is same as Example 1 except:

In step 2: benzaldehyde is replaced by 3-methylbenzaldehyde

In step 4: (3-chlorophenyl)methanamine is replaced by (2-(trifluoromethyl)phenyl)methanamine I-31 (yield 26%), $^1$HNMR (DMSO_d6), δ 2.29 (s, 3H), 2.60 (t, J=4.8 Hz, 2H), 2.65 (d, J=4.8 Hz, 2H), 3.03 (s, 2H), 3.59 (s, 2H), 3.67 (t, J=8.8 Hz, 2H), 3.99 (t, J=8.8 Hz, 2H), 5.10 (s, 2H), 7.06-7.14 (m, 4H), 7.21 (t, J=7.2 Hz, 1H), 7.45 (t, J=7.6 Hz, 1H), 7.59 (t, J=7.6 Hz, 1H), 7.73 (t, J=8.0 Hz, 1H); LC-MS: m/z=455.2(M+1).

EXAMPLE 32

Synthesis of Compound I-32

4-(2-chlorobenzyl)-7-(3-methylbenzyl)-1,2,6,7,8,9-hexahydroimidazo[1,2-a]pyrido[3,4-e]pyrimidin-5(4H)-one

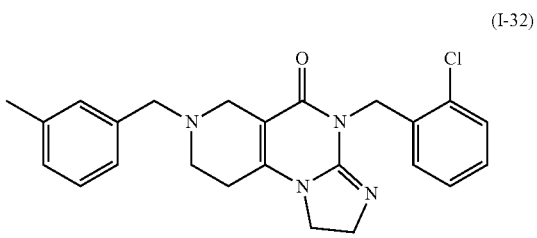 [SMILES: Cc1cccc(CN2CCC3=C(C2)C(=O)N(Cc2ccccc2F)C2=NCCN23)c1]
(I-32)

The procedure is same as Example 1 except:

In step 2: benzaldehyde is replaced by 3-methylbenzaldehyde

In step 4: (3-chlorophenyl)methanamine is replaced by (2-chlorophenyl)methanamine I-32 (yield 26%), $^1$HNMR (DMSO_d6), δ 2.29 (s, 3H), 2.57 (s, 2H), 2.64 (d, J=5.2 Hz, 2H), 3.04 (s, 2H), 3.58 (s, 2H), 3.67 (t, J=9.2 Hz, 2H), 3.98 (t, J=9.2 Hz, 2H), 4.96 (s, 2H), 6.95 (t, J=4.0 Hz, 1H), 7.06-7.14 (m, 3H), 7.21-7.28 (m, 3H), 7.43-7.46 (m, 1H); LC-MS: m/z=421.2(M+1).

EXAMPLE 33

Synthesis of Compound I-33

4-(2-bromobenzyl)-7-(3-methylbenzyl)-1,2,6,7,8,9-hexahydroimidazo[1,2-a]pyrido[3,4-e]pyrimidin-5(4H)-one

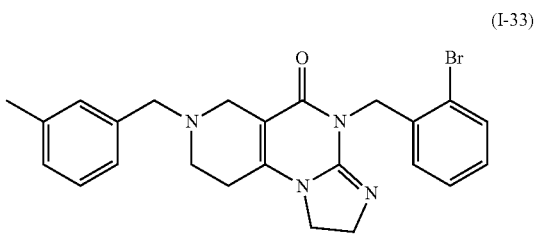 [SMILES: Cc1cccc(CN2CCC3=C(C2)C(=O)N(Cc2ccccc2Br)C2=NCCN23)c1]
(I-33)

The procedure is same as Example 1 except:

In step 2: benzaldehyde is replaced by 3-methylbenzaldehyde

In step 4: (3-chlorophenyl)methanamine is replaced by (2-bromophenyl)methanamine I-33 (yield 28%), $^1$HNMR (DMSO_d6), δ 2.30 (s, 3H), 2.57-2.65 (m, 4H), 3.04 (s, 2H), 3.59-3.67 (m, 4H), 3.98 (s, 2H), 4.91 (s, 2H), 6.91 (s, 1H), 7.13-7.31 (m, 6H), 7.61 (s, 1H); LC-MS: m/z=466.1(M+1).

EXAMPLE 34

Synthesis of Compound I-34

4-(2-methylbenzyl)-7-(3-methylbenzyl)-1,2,6,7,8,9-hexahydroimidazo[1,2-a]pyrido[3,4-e]pyrimidin-5(4H)-one

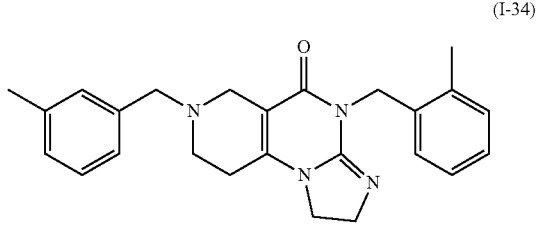 [SMILES: Cc1cccc(CN2CCC3=C(C2)C(=O)N(Cc2ccccc2C)C2=NCCN23)c1]

(I-34)

The procedure is same as Example 1 except:

In step 2: benzaldehyde is replaced by 3-methylbenzaldehyde

In step 4: (3-chlorophenyl)methanamine is replaced by o-tolylmethanamine

I-34 (yield 22%), $^1$HNMR(CD$_3$OD), δ 2.34 (s, 3H), 2.37 (s, 3H), 2.58 (d, J=5.2 Hz, 2H), 2.73 (t, J=5.6 Hz, 2H), 3.22 (s, 2H), 3.65 (s, 2H), 3.79 (t, J=9.2 Hz, 2H), 3.99 (t, J=9.2 Hz, 2H), 5.00 (s, 1H), 6.89 (d, J=3.6 Hz, 1H), 7.05-7.25 (m, 7H); LC-MS: m/z=401.2(M+1).

EXAMPLE 35

Synthesis of Compound I-35

7-(3-chlorobenzyl)-4-(2-(trifluoromethyl)benzyl)-1,2,6,7,8,9-hexahydroimidazo[1,2-a]pyrido[3,4-e]pyrimidin-5(4H)-one

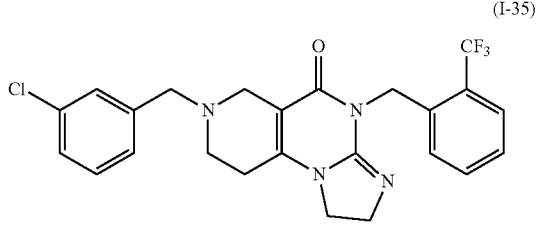 [SMILES: O=C1C2=C(CCN(Cc3cccc(Cl)c3)C2)N2CCN=C2N1Cc1ccccc1C(F)(F)F]

(I-35)

The procedure is same as Example 1 except:

In step 2: benzaldehyde is replaced by 3-chlorobenzaldehyde

In step 4: (3-chlorophenyl)methanamine is replaced by (2-(trifluoromethyl)phenyl)methanamine I-35 (yield 26%), $^1$HNMR (DMSO_d6), δ 2.60 (s, 2H), 2.67 (d, J=5.2 Hz, 2H), 3.06 (s, 2H), 3.68 (m, 4H), 3.99 (t, J=8.8 Hz, 2H), 5.10 (s, 2H), 7.08 (d, J=5.2 Hz, 1H), 7.29-7.39 (m, 4H), 7.45 (t, J=7.6 Hz, 1H), 7.59 (t, J=7.6 Hz, 1H), 7.73(d, J=7.6 Hz, 1H); LC-MS: m/z=475.1(M+1).

EXAMPLE 36

Synthesis of Compound I-36

4-(2-chlorobenzyl)-7-(3-chlorobenzyl)-1,2,6,7,8,9-hexahydroimidazo[1,2-a]pyrido[3,4-e]pyrimidin-5(4H)-one

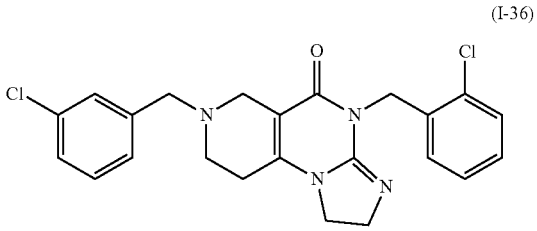 [SMILES: O=C1C2=C(CCN(Cc3cccc(Cl)c3)C2)N2CCN=C2N1Cc1ccccc1Cl]

(I-36)

The procedure is same as Example 1 except:

In step 2: benzaldehyde is replaced by 3-chlorobenzaldehyde

In step 4: (3-chlorophenyl)methanamine is replaced by (2-chlorophenyl)methanamine I-36 (yield 28%), $^1$HNMR (DMSO_d6), δ 2.58 (s, 2H), 2.66 (t, J=5.2 Hz, 2H), 3.07 (s, 2H), 3.67 (m, 4H), 3.99 (t, J=9.2 Hz, 2H), 4.96 (s, 2H), 6.96 (t, J=4.4 Hz, 1H), 7.26-7.43 (m, 6H), 7.45 (t, J=3.6 Hz, 1H); LC-MS: m/z=441.1 (M+1).

EXAMPLE 37

Synthesis of Compound I-37

4-(2-bromobenzyl)-7-(3-chlorobenzyl)-1,2,6,7,8,9-hexahydroimidazo[1,2-a]pyrido[3,4-e]pyrimidin-5(4H)-one

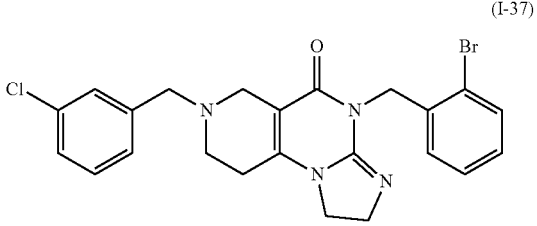 [SMILES: O=C1C2=C(CCN(Cc3cccc(Cl)c3)C2)N2CCN=C2N1Cc1ccccc1Br]

(I-37)

The procedure is same as Example 1 except:

In step 2: benzaldehyde is replaced by 3-chlorobenzaldehyde

In step 4: (3-chlorophenyl)methanamine is replaced by (2-bromophenyl)methanamine I-37 (yield 29%), $^1$HNMR (DMSO_d6), δ 2.58 (s, 2H), 2.66 (t, J=4.8 Hz, 2H), 3.06 (s, 2H), 3.67 (m, 4H), 3.99 (t, J=8.8 Hz, 2H), 4.91(s, 2H), 6.91 (d, J=7.2 Hz, 1H), 7.19 (t, J=7.2 Hz, 1H), 7.29-7.39 (m, 5H), 7.61 (d, J=7.6 Hz, 1H); LC-MS: m/z=487.1(M+1).

EXAMPLE 38

Synthesis of Compound I-38

7-benzyl-4-(3-(trifluoromethyl)benzyl)-1,2,6,7,8,9-hexahydroimidazo[1,2-a]pyrido[3,4-e]pyrimidin-5(4H)-one

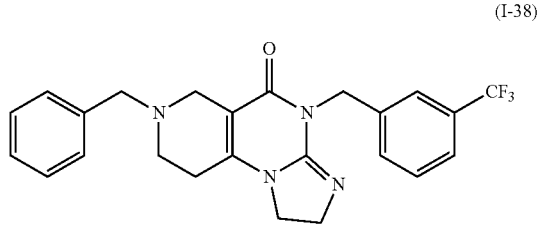
(I-38)

The procedure is same as Example 1 except:

In step 4: (3-chlorophenyl)methanamine is replaced by (3-(trifluoromethyl)phenyl)methanamine I-38 (yield 20%), $^1$HNMR(CD$_3$OD), δ 2.55 (t, J=3.6 Hz, 2H), 2.71 (t, J=4 Hz, 2H), 3.23 (s, 2H), 3.68 (s, 2H), 3.84 (t, J=6.4 Hz, 2H), 3.99 (t, J=6.4 Hz, 2H), 5.07 (s, 2H), 7.27 (t, 4.4 Hz, 1H), 7.32-7.37 (m, 4H), 7.47 (t, J=5.2 Hz, 1H), 7.54 (d, J=5.2 Hz, 1H), 7.61 (d, J=5.6 Hz, 1H), 7.68 (s, 1H); LC-MS: m/z=441.2(M+1).

EXAMPLE 39

Synthesis of Compound I-39

7-benzyl-4-(4-(trifluoromethyl)benzyl)-1,2,6,7,8,9-hexahydroimidazo[1,2-a]pyrido[3,4-e]pyrimidin-5(4H)-one

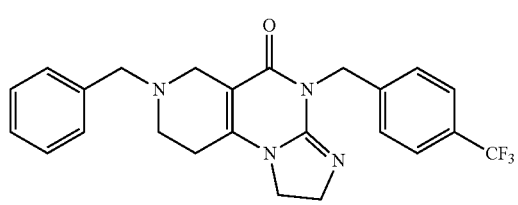
(I-39)

The procedure is same as Example 1 except:

In step 4: (3-chlorophenyl)methanamine is replaced by (4-(trifluoromethyl)phenyl)methanamine I-39 (yield 18%), $^1$HNMR(CD$_3$OD), δ 2.61 (t, J=4.0 Hz, 2H), 2.76 (t, J=4.0 Hz, 2H), 3.24 (s, 2H), 3.72 (s, 2H), 3.86 (t, J=6.4 Hz, 2H), 4.05 (t, J=6.4 Hz, 2H), 5.10 (s, 2H), 7.28-7.39 (m, 5H), 7.50 (d, J=5.2 Hz, 2H), 7.60 (d, J=5.2 Hz, 2H); LC-MS: m/z=441.2(M+1).

EXAMPLE 40

Synthesis of Compound I-40

7-benzyl-4-(3,4-dichlorobenzyl)-1,2,6,7,8,9-hexahydroimidazo[1,2-a]pyrido[3,4-e]pyrimidin-5(4H)-one

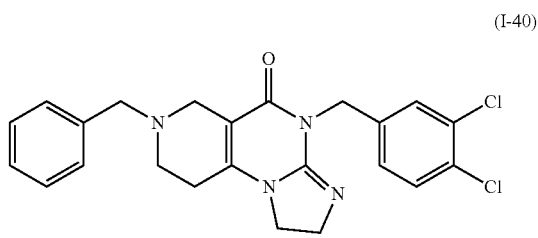 [SMILES: O=C1C2=C(CCN(Cc3ccccc3)C2)N2CCN=C2N1Cc1ccc(Cl)c(Cl)c1]
(I-40)

The procedure is same as Example 1 except:

In step 4: (3-chlorophenyl)methanamine is replaced by (3,4-dichlorophenyl)methanamine I-40 (yield 20%), $^1$HNMR(CD$_3$OD), δ 2.60 (s, 2H), 2.76 (s, 2H), 3.24 (s, 2H), 3.72 (s, 2H), 3.87 (t, J=6.0 Hz, 2H), 4.05 (t, J=6.0 Hz, 2H), 4.98 (s, 2H), 7.28-7.39 (m, 6H), 7.44 (d, J=5.6 Hz, 1H), 7.50 (s, 1H); LC-MS: m/z=441.1(M+1).

EXAMPLE 41

Synthesis of Compound I-41

7-benzyl-4-(2,4-dichlorobenzyl)-1,2,6,7,8,9-hexahydroimidazo[1,2-a]pyrido[3,4-e]pyrimidin-5(4H)-one

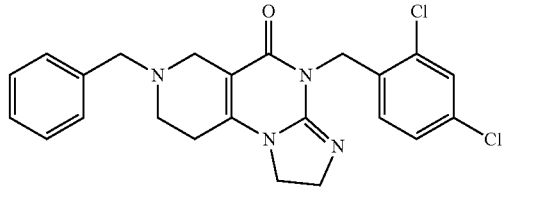
(I-41)

The procedure is same as Example 1 except:

In step 4: (3-chlorophenyl)methanamine is replaced by (2,4-dichlorophenyl)methanamine I-41 (yield 19%), $^1$HNMR(CD$_3$OD), δ 2.60 (s, 2H), 2.66 (t, J=6.8 Hz, 2H), 3.05 (s, 2H), 3.64 (s, 2H), 3.68 (t, J=6.0 Hz, 2H), 3.98 (t, J=6.0 Hz, 2H), 4.93 (s, 2H), 6.99 (d, J=5.6 Hz, 1H), 7.27 (d, J=4.0 Hz, 1H), 7.33-7.37 (m, 5H), 7.62 (s, 1H); LC-MS: m/z=441.1(M+1).

EXAMPLE 42

Synthesis of Compound I-42

7-benzyl-4-(4-chloro-3-(trifluoromethyl)benzyl)-1,2,6,7,8,9-hexahydroimidazo[1,2-a]pyrido[3,4-e]pyrimidin-5(4H)-one

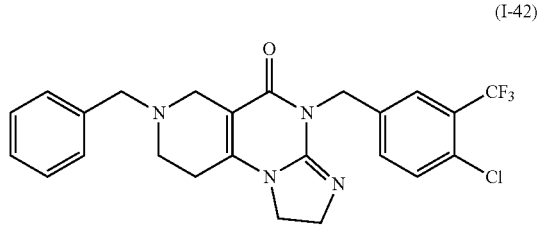 [SMILES: O=C1C2=C(CCN(Cc3ccccc3)C2)N2CCN=C2N1Cc1ccc(Cl)c(C(F)(F)F)c1]

(I-42)

The procedure is same as Example 1 except:

In step 4: (3-chlorophenyl)methanamine is replaced by (4-chloro-3-(trifluoromethyl)phenyl)methanamine I-42 (yield 15%), $^1$HNMR(CD$_3$OD), δ 2.52 (t, J=4.0 Hz, 2H), 2.69 (d, J=4.0 Hz, 2H), 3.21 (s, 2H), 3.66 (s, 2H), 3.84 (t, J=6.4 Hz, 2H), 3.96 (t, J=6.4 Hz, 2H), 5.02 (s, 2H), 7.25-7.35 (m, 5H), 7.49 (d, J=5.6 Hz, 1H), 7.58 (d, J=5.6 Hz, 1H), 7.81 (s, 1H); LC-MS: m/z=475.1(M+1).

EXAMPLE 43

Synthesis of Compound I-43

7-benzyl-4-(4-chloro-2-(trifluoromethyl)benzyl)-1,2,6,7,8,9-hexahydroimidazo[1,2-a]pyrido[3,4-e]pyrimidin-5(4H)-one

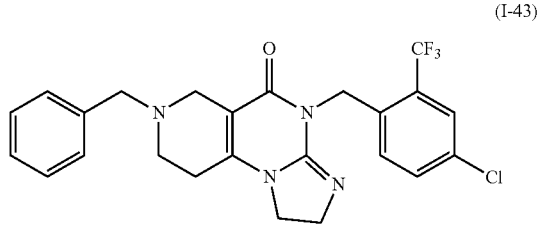

(I-43)

The procedure is same as Example 1 except:

In step 4: (3-chlorophenyl)methanamine is replaced by (4-chloro-2-(trifluoromethyl)phenyl)methanamine I-43 (yield 18%), $^1$HNMR(CD$_3$OD), δ 2.66 (t, J=5.6 Hz, 2H), 2.79 (t, J=5.6 Hz, 2H), 3.23 (s, 2H), 3.72 (s, 2H), 3.84 (t, J=9.2 Hz, 2H), 4.09 (t, J=9.2 Hz, 2H), 5.21 (s, 2H), 7.18 (d, J=8.8 Hz, 1H), 7.29-7.39 (m, 5H), 7.56 (d, J=8.8 Hz, 1H), 7.73 (d, J=1.6 Hz, 1H); LC-MS: m/z=475.1(M+1).

EXAMPLE 44

Synthesis of Compound I-44

7-(4-tert-butylbenzyl)-4-(2-methylbenzyl)-1,2,6,7,8,9-hexahydroimidazo[1,2-a]pyrido[3,4-e]pyrimidin-5(4H)-one

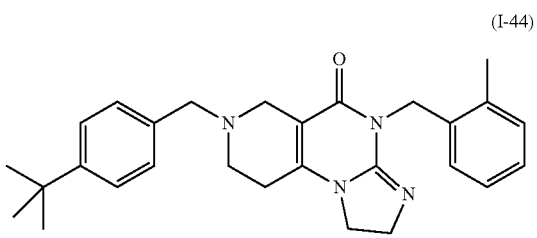 [SMILES: Cc1ccccc1CN1C(=O)C2=C(CCN(Cc3ccc(C(C)(C)C)cc3)C2)N2CCN=C12]

(I-44)

The procedure is same as Example 1 except:

In step 2: benzaldehyde is replaced by 4-tert-butylbenzaldehyde

In step 4: (3-chlorophenyl)methanamine is replaced by o-tolylmethanamine

I-44 (yield 25%), $^1$HNMR (DMSO_d6), δ 2.31 (s, 3H), 2.56 (s, 2H), 2.64 (d, J=4 Hz, 2H), 3.02 (s, 2H), 3.58 (s, 2H), 3.68 (t, J=8.8 Hz, 2H), 3.97 (t, J=8.8 Hz, 2H), 4.87(s, 2H), 6.89 (d, J=6.8 Hz, 1H), 7.10 (m, 3H), 7.24 (d, J=6.8 Hz, 2H), 7.35 (d, J=6.8 Hz, 1H). LC-MS: m/z=443.2(M+1).

EXAMPLE 45

Synthesis of Compound I-45

4-(2-chlorobenzyl)-7-(2-methylbenzyl)-1,2,6,7,8,9-hexahydroimidazo[1,2-a]pyrido[3,4-e]pyrimidin-5(4H)-one

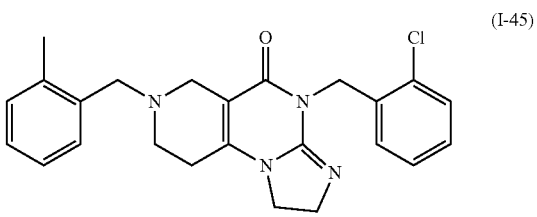

(I-45)

The procedure is same as Example 1 except:

In step 2: benzaldehyde is replaced by 2-methylbenzaldehyde

In step 4: (3-chlorophenyl)methanamine is replaced by (2-chlorophenyl)methanamine I-45 (yield 22%), $^1$HNMR (DMSO_d6), δ 2.32 (s, 3H), 2.56 (m, 2H), 2.67 (t, J=5.6 Hz, 2H), 3.07 (s, 2H), 3.60 (s, 2H), 3.67 (t, J=8.4 Hz, 2H), 3.98 (t, J=9.2 Hz, 2H), 4.96 (s, 2H), 6.94-6.96 (m, 1H), 7.16-7.21 (m, 3H), 7.25-7.28 (m, 3H), 7.43-7.46 (m, 1H). LC-MS: m/z=421.1(M+1).

EXAMPLE 46

Synthesis of Compound I-46

4-(2-bromobenzyl)-7-(2-methylbenzyl)-1,2,6,7,8,9-hexahydroimidazo[1,2-a]pyrido[3,4-e]pyrimidin-5(4H)-one

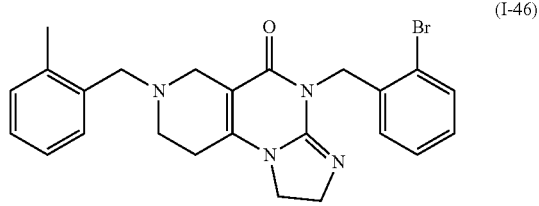

(I-46)

The procedure is same as Example 1 except:

In step 2: benzaldehyde is replaced by 2-methylbenzaldehyde

In step 4: (3-chlorophenyl)methanamine is replaced by (2-bromophenyl)methanamine I-46 (yield 25%), ¹HNMR (DMSO_d6) δ 2.32 (s, 3H), 2.56 (s, 2H), 2.67 (t, J=5.2 Hz, 2H), 3.07 (s, 2H), 3.59 (s, 2H), 3.67 (t, J=9.2 Hz, 2H), 3.98 (t, J=9.2 Hz, 2H), 4.90 (s, 2H), 6.90 (d, J=3.6 Hz, 1H), 7.13-7.33 (m, 6H), 7.61 (d, J=8.0 Hz, 1H); LC-MS: m/z=464.1, 466.1(M+1).

EXAMPLE 47

Synthesis of Compound I-47

4,7-bis(2-methylbenzyl)-1,2,6,7,8,9-hexahydroimidazo[1,2-a]pyrido[3,4-e]pyrimidin-5(4H)-one

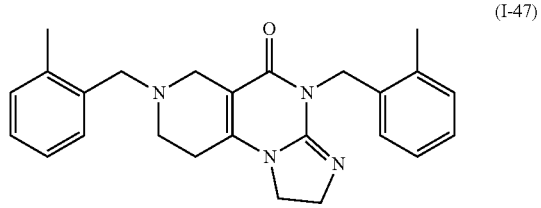

(I-47)

The procedure is same as Example 1 except:

In step 2: benzaldehyde is replaced by 2-methylbenzaldehyde

In step 4: (3-chlorophenyl)methanamine is replaced by o-tolylmethanamine

I-47(yield 19%), ¹HNMR(CD₃OD) δ 2.34 (s, 3H), 2.39 (s, 3H), 2.59 (s, 2H), 2.75 (t, J=5.2 Hz, 2H), 3.24 (s, 2H), 3.67 (s, 2H), 3.80 (t, J=9.2 Hz, 2H), 4.02 (t, J=9.2 Hz, 2H), 5.00 (s, 2H), 6.89 (d, J=7.2 Hz, 1H), 7.07-7.30 (m, 7H); LC-MS: m/z=401.2(M+1).

EXAMPLE 48

Synthesis of Compound I-48

4-(2-bromobenzyl)-7-(3-bromobenzyl)-1,2,6,7,8,9-hexahydroimidazo[1,2-a]pyrido[3,4-e]pyrimidin-5(4H)-one

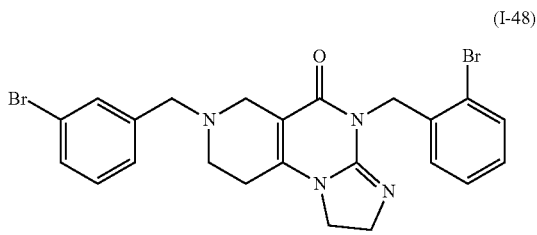 [SMILES: O=C1C2=C(CCN(Cc3cccc(Br)c3)C2)N2CCN=C2N1Cc1ccccc1Br]

(I-48)

The procedure is same as Example 1 except:

In step 2: benzaldehyde is replaced by 3-bromobenzaldehyde

In step 4: (3-chlorophenyl)methanamine is replaced by (2-bromophenyl)methanamine I-48 (yield 40%), ¹HNMR (DMSO_d6) δ 2.59 (t, J=4.0 Hz, 2H), 2.66 (t, J=5.2 Hz, 2H), 3.06 (s, 2H), 3.67 (m, 4H), 3.98 (t, J=9.2 Hz, 2H), 4.90 (s, 2H), 6.91 (d, J=7.2 Hz, 1H), 7.20 (t, J=6.8 Hz, 1H), 7.29-7.35 (m, 3H), 7.46 (d, J=6.8 Hz, 1H), 7.54 (s, 1H), 7.62 (d, J=7.6 Hz, 1H). LC-MS: m/z=531.0(M+1).

EXAMPLE 49

Synthesis of Compound I-49

4-(2-fluorobenzyl)-7-(3-fluorobenzyl)-1,2,6,7,8,9-hexahydroimidazo[1,2-a]pyrido[3,4-e]pyrimidin-5(4H)-one

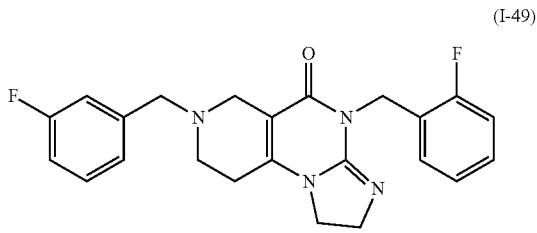 [SMILES: O=C1C2=C(CCN(Cc3cccc(F)c3)C2)N2CCN=C2N1Cc1ccccc1F]

(I-49)

The procedure is same as Example 1 except:

In step 2: benzaldehyde is replaced by 3-fluorobenzaldehyde

In step 4: (3-chlorophenyl)methanamine is replaced by (3-fluorophenyl)methanamine I-49 (yield 20%), ¹HNMR (DMSO_d6), \ δ 2.56 (d, J=4.8 Hz, 2H), 2.65 (t, J=4.8 Hz, 2H), 3.06 (s, 2H) 3.65 (s, 2H), 3.69 (t, J=9.2 Hz, 2H), 3.97 (t, J=9.2 Hz, 2H), 4.96 (s, 2H), 7.07-7.18 (m, 6H), 7.26-7.29 (m, 1H), 7.35-7.39 (m, 1H); LC-MS: m/z=409.1(M+1).

EXAMPLE 50

Synthesis of Compound I-50

7-(3-fluorobenzyl)-4-(2-(trifluoromethyl)benzyl)-1,2,6,7,8,9-hexahydroimidazo[1,2-a]pyrido[3,4-e]pyrimidin-5(4H)-one

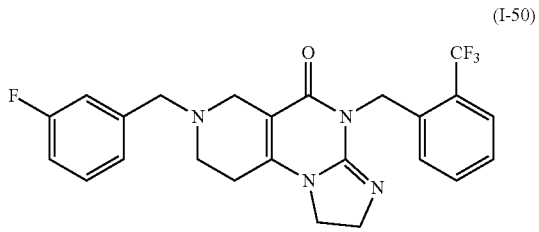

(I-50)

The procedure is same as Example 1 except:

In step 2: benzaldehyde is replaced by 3-fluorobenzaldehyde

In step 4: (3-chlorophenyl)methanamine is replaced by (2-(trifluoromethyl)phenyl)methanamine I-50 (yield 22%), $^1$HNMR (DMSO_d6) δ 2.60 (t, J=4.4 Hz, 2H), 2.67 (t, J=4.4 Hz, 2H), 3.07 (s, 2H), 3.68 (m, 4H), 34.00 (t, J=8.8 Hz, 2H), 5.10 (s, 2H), 7.07-7.18 (m, 4H), 7.35-7.47 (m, 2H), 7.60 (t, J=7.6 Hz, 1H), 7.73 (d, J=8.0 Hz, 1H); LC-MS: m/z=459.1(M+1).

EXAMPLE 51

Synthesis of Compound I-51

4-(2-chlorobenzyl)-7-(3-fluorobenzyl)-1,2,6,7,8,9-hexahydroimidazo[1,2-a]pyrido[3,4-e]pyrimidin-5(4H)-one

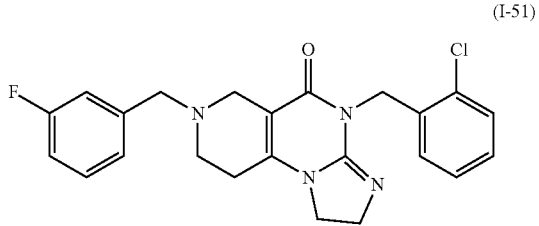 [SMILES: O=C1C2=C(CCN(Cc3cccc(F)c3)C2)N2CCN=C2N1Cc1ccccc1Cl]

(I-51)

The procedure is same as Example 1 except:

In step 2: benzaldehyde is replaced by 3-fluorobenzaldehyde

In step 4: (3-chlorophenyl)methanamine is replaced by (2-chlorophenyl)methanamine I-51 (yield 30%), $^1$HNMR (DMSO_d6) δ 2.58 (t, J=3.6 Hz, 2H), 2.67 (t, J=5.2 Hz, 2H), 3.07 (s, 2H), 3.68 (m, 4H), 3.99 (t, J=8.8 Hz, 2H), 4.96 (s, 2H), 6.94-6.96 (m, 1H), 7.07-7.18 (m, 3H), 7.25-7.29 (m, 2H), 7.35-7.46 (m, 2H); LC-MS: m/z=425.1(M+1).

EXAMPLE 52

Synthesis of Compound I-52

4-(2-bromobenzyl)-7-(3-fluorobenzyl)-1,2,6,7,8,9-hexahydroimidazo[1,2-a]pyrido[3,4-e]pyrimidin-5(4H)-one

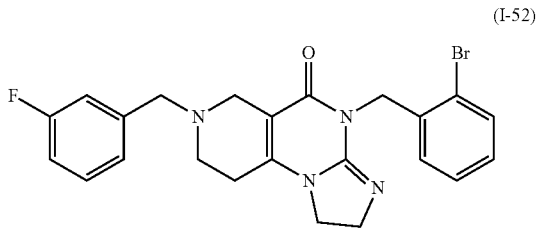 [SMILES: O=C1C2=C(CCN(Cc3cccc(F)c3)C2)N2CCN=C2N1Cc1ccccc1Br]

(I-52)

The procedure is same as Example 1 except:

In step 2: benzaldehyde is replaced by 3-fluorobenzaldehyde

In step 4: (3-chlorophenyl)methanamine is replaced by (2-bromophenyl)methanamine I-52 (yield 30%), $^1$HNMR (DMSO_d6) δ 2.58 (s, 2H), 2.65 (t, J=4.8 Hz, 2H), 3.07 (s, 2H), 3.68 (m, 4H), 3.98 (t, J=8.8 Hz, 2H), 4.91 (s, 2H), 6.91 (d, J=7.6 Hz, 1H), 7.07-7.21 (m, 4H), 7.30-7.41 (m, 2H), 7.62 (d, J=7.6 Hz, 1H); LC-MS: m/z=470.1(M+1).

EXAMPLE 53

Synthesis of Compound I-53

7-(3-bromobenzyl)-4-(2-fluorobenzyl)-1,2,6,7,8,9-hexahydroimidazo[1,2-a]pyrido[3,4-e]pyrimidin-5(4H)-one

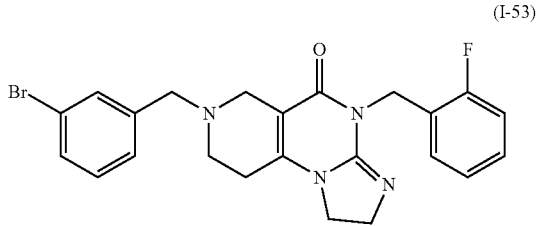

(I-53)

The procedure is same as Example 1 except:

In step 2: benzaldehyde is replaced by 3-bromobenzaldehyde

In step 4: (3-chlorophenyl)methanamine is replaced by (2-fluorophenyl)methanamine I-53 (yield 29%) $^1$HNMR (DMSO_d6) δ 2.62 (t, J=4.8 Hz, 2H), 2.72 (t, J=5.2 Hz, 2H), 3.11 (s, 2H), 3.69 (s, 2H), 3.75 (t, J=9.2 Hz, 4H), 4.03 (t, J=9.2 Hz, 2H), 5.02 (s, 2H), 7.16-7.24 (m, 3H), 7.34-7.40 (m, 3H), 7.52 (d, J=7.2 Hz, 1H), 7.59 (s, 1H); LC-MS: m/z=470.1(M+1).

EXAMPLE 54

Synthesis of Compound I-54

7-(3-bromobenzyl)-4-(2-(trifluoromethyl)benzyl)-1,2,6,7,8,9-hexahydroimidazo[1,2-a]pyrido[3,4-e]pyrimidin-5(4H)-one (I-54)

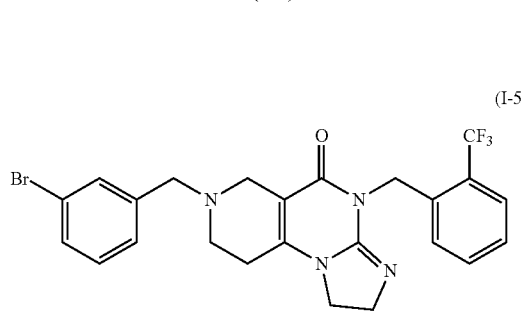

The procedure is same as Example 1 except:

In step 2: benzaldehyde is replaced by 3-bromobenzaldehyde

In step 4: (3-chlorophenyl)methanamine is replaced by (2-(trifluoromethyl)phenyl)methanamine I-54 (yield 30%), $^1$HNMR (DMSO_d6) δ 2.59 (s, 2H), 2.67 (t, J=4.8 Hz, 2H), 3.01 (s, 2H), 3.67 (m, 4H), 3.99 (t, J=9.2 Hz, 2H), 5.10 (s, 2H), 7.08 (d, J=8.0 Hz, 1H), 7.28-7.35 (m, 2H), 7.43-7.47 (m, 2H), 7.53-7.61 (m, 2H), 7.73 (d, J=7.6 Hz, 1H); LC-MS: m/z=520.1(M+1).

EXAMPLE 55

Synthesis of Compound I-55

2-Benzyl-5-(2-bromobenzyl)-2,3,7,8-tetrahydro-1H-imidazo[1,2-a]pyrrolo[3,4-e]pyrimidin-4(5H)-one

I-55

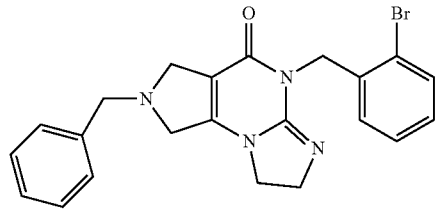

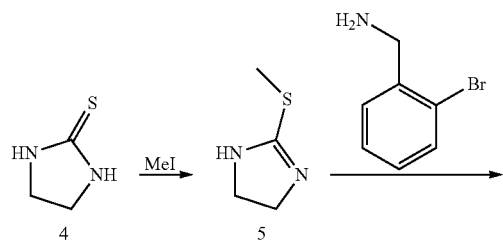

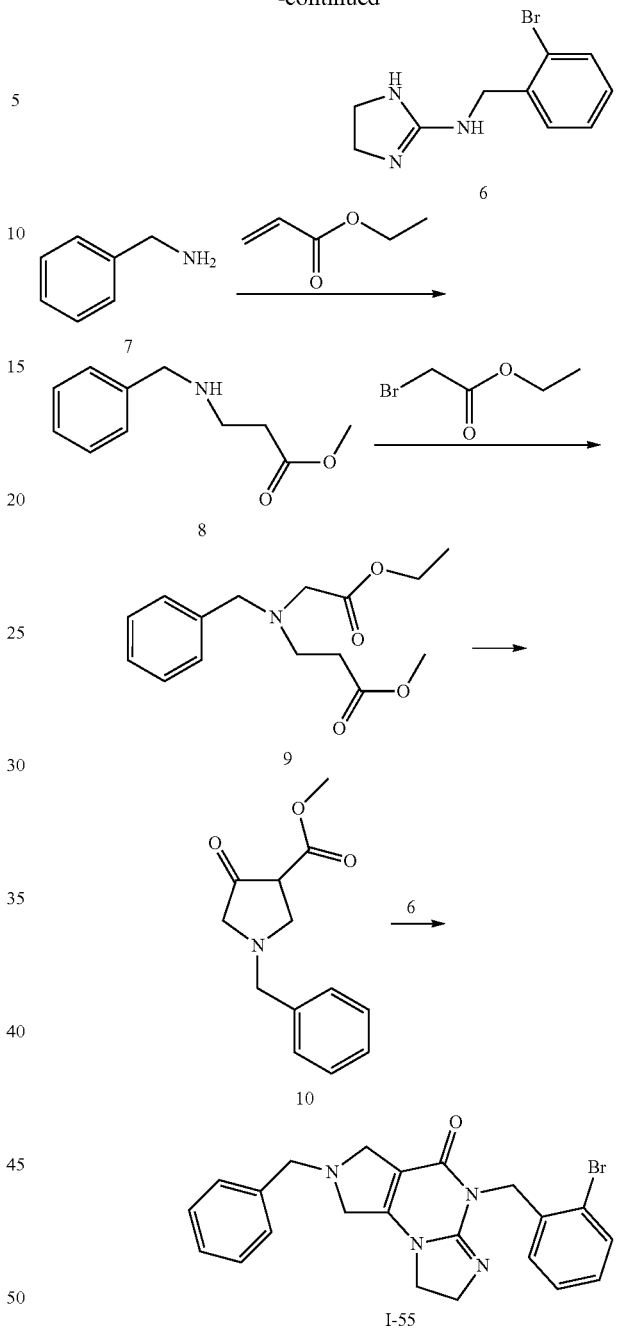

Step 1: Imidazolidine-2-thione 4(59.8 mmol) was dissolved in methanol (70 ml), iodomethane (89.7 mmol) was added dropwise at 25° C. and the solution was refluxed for 30 minutes. The solvent was removed under vacuum, and the residue was stirred with tert-butyl methyl ether, and the suspension was filtered and the filtered cake was dried under vacuum to afford compound 5 (yield 83%).

Step 2: Compound 5 (2 mmol) was dissolved in dioxane (5 ml, and (2-bromophenyl)methanamine (4.2 mmol) was added. The mixture was refluxed for 12 h. LCMS confirmed the reaction completed. The mixture was cooled down to room temperature. Solvent was removed under vacuum. The residue was stirred with toluene for 8 h. The suspension was filtered. The filtered cake was dried under vacuum to afford compound 6.

Step 3: To a mixture of phenylmethanamine (458 mmol) and ethyl acrylate (458 mmol) in dichloromethane (500 ml), a solution of 2,2,2-trifluoroacetic acid (87.7 mmol) in dichloromethane (30 ml) was added dropwise under 10° C. The reaction was kept for 2 h at 10-15° C. LC-MS confirmed the reaction was completed. The mixture was washed with saturated Na$_2$CO$_3$ solution, and the organic layer was separated, dried over Na$_2$SO$_4$, and concentrated. Compound 8 was obtained as yellow oil (85 g, 96.2%).

Step 4: To a solution of compound 8 (114.9 mmol) in acetonitrile (300 ml) K$_2$CO$_3$ (290 mmol) was added. The mixture was heated at 60° C., then ethyl 2-bromoacetate (144.6 mmol) was added dropwise. The mixture was reacted for 6 h at 60° C. LC-MS confirmed the reaction was completed. The mixture was cooled to room temperature. Dichloromethane was added, and the solution was washed with water three times. The organic layer was separated, dried over Na$_2$SO$_4$, concentrated under vacuum to afford compound 9 as yellow oil (40 g, 93.7%).

Step 5: To a solution of t-BuOK (136.6 mmol) in THF (150 ml) at −78° C. under N$_2$, compound 9 (68.3 mmol) was added dropwise. The reaction was kept at −78° C. for 3 h. LC-MS confirmed that the reaction was completed. The reaction was quenched with water (300 mL), washed with ethyl acetate (150 mL) once. The aqueous layer was slowly added with NaCl until it was saturated. The system was stirred for 30 min at room temperature. White solid came out, filtered, and dried under vacuum. Compound 10 was obtained as white solid (8 g, 61.5%).

Step 6: Compound 10 (0.86 mmol) was dissolved in toluene (4 mL), compound 6 (0.9 mmol), t-BuOK (2.58 mmol) was added. The mixture was refluxed for 12 h. LC-MS confirmed the reaction was completed. The mixture was dissolved in ethyl acetate, washed with water, the organic phase was separated and concentrated. The residue was purified by TLC plate to afford desired product (10 mg, 2.7%).

$^1$HNMR (CD$_3$OD) δ 3.59 (m, 4H), 3.68 (s, 2H), 3.76 (t, J=9.6 Hz, 2H), 3.92 (t, J=9.6 Hz, 2H), 4.84 (s, 2H), 7.13-7.19 (m, 7H), 7.27-7.28 (m, 1H), 7.51 (d, J=8.0 Hz, 1H); LC-MS: m/z=436.1(M+1).

EXAMPLE 56

Synthesis of Compound I-56

2-benzyl-5-(2,4-dichlorobenzyl)-2,3,7,8-tetrahydro-1H-imidazo[1,2-a]pyrrolo[3,4-e]pyrimidin-4(5H)-one

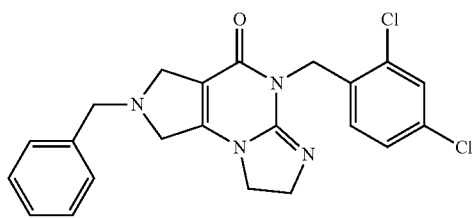

(I-56)

The procedure is same as Example 55 except:

In step 2: (2-bromophenyl)methanamine is replaced by (2,4-dichlorophenyl)methanamine I-56 (yield 3.2%), $^1$HNMR (CD$_3$OD) δ 3.73(m, 4H), 3.81-3.89 (m, 4H), 4.03 (t, J=8.4 Hz, 2H), 4.96 (s, 2H), 7.21-7.52 (m, 7H), 7.52 (d, J=2.4 Hz, 1H); LC-MS: m/z=427.1(M+1).

EXAMPLE 57

Synthesis of Compound I-57

2-benzyl-5-(4-chloro-3-(trifluoromethyl)benzyl)-2,3,7,8-tetrahydro-1H-imidazo[1,2-a]pyrrolo[3,4-e]pyrimidin-4(5H)-one

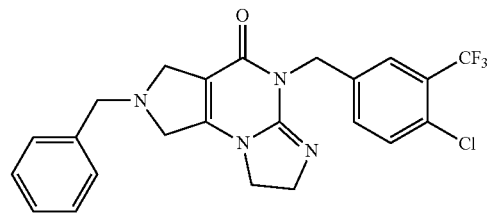

(I-57)

The procedure is same as Example 55 except:

In step 2: (2-bromophenyl)methanamine is replaced by (4-chloro-3-(trifluoromethyl)phenyl)methanamine I-57 (yield 3.0%), $^1$HNMR(CD$_3$OD) δ 3.69 (s, 2H), 3.78-3.89 (m, 4H), 3.87 (m, 2H), 4.01 (m, 2H), 4.93(s, 2H), 7.25-7.33 (m, 5H), 7.51 (d, J=8.4 Hz, 1H), 7.61 (d, J=8.4 Hz, 1H), 7.70 (s, 1H); LC-MS: m/z=461.1(M+1).

EXAMPLE 58

Synthesis of Compound I-58

2-benzyl-5-(2-methylbenzyl)-2,3,7,8-tetrahydro-1H-imidazo[1,2-a]pyrrolo[3,4-e]pyrimidin-4(5H)-one

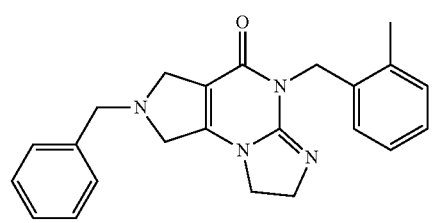

(I-58)

The procedure is same as Example 55 except:

In step 2: (2-bromophenyl)methanamine is replaced by o-tolylmethanamine

I-58 (yield 2.8%), $^1$HNMR (CD$_3$OD) δ 2.26 (s, 3H), 3.65-3.69 (m, 4H), 3.75 (s, 2H), 3.82 (t, J=8.8 Hz, 2H), 4.01 (t, J=8.8 Hz, 2H), 4.87 (s, 2H), 6.99 (d, J=4.8 Hz, 1H), 7.16-7.27 (m, 8H); LC-MS: m/z=373.2(M+1).

COMPARISON EXAMPLE

Synthesis of TIC10

7-benzyl-4-(2-methylbenzyl)-1,2,6,7,8,9-hexahydroimidazo[1,2-a]pyrido[3,4-e]pyrimidin-5(4H)-one (TIC10)

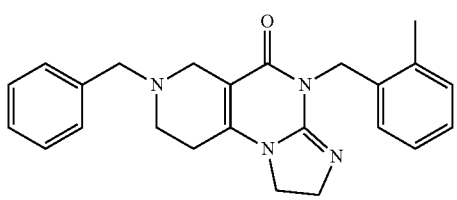

Step 1: Synthesis of N-(2-methylbenzyl)-4,5-dihydro-1H-imidazol-2-amine

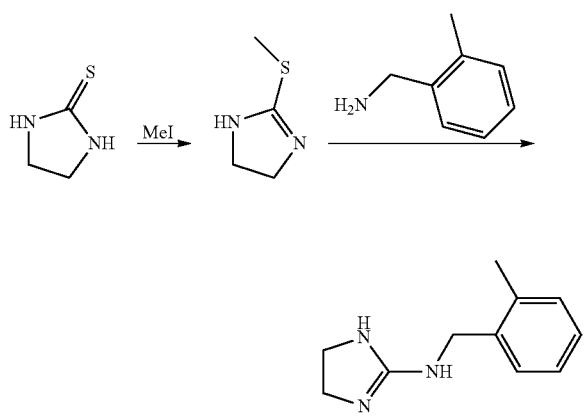

Imidazolidine-2-thione (6.93 g, 59.8 mmol) was dissolved in methanol (70 mL), iodomethane (12.9 g, 89.7 mmol) was added dropwise at 25° C. The reaction was refluxed for 30 minutes and the solvent was removed under vacuum. The residue was stirred with tert-tutyl methyl ether, filtered, and dried under vacuum to give 2-(methylthio)-4,5-dihydro-1H-imidazole (12.8 g, yield 83%) as white solid.

A mixture of 2-(methylthio)-4,5-dihydro-1H-imidazole (516.2 mg, 2 mmol) and o-tolylmethanamine (508.6 mg, 4.2 mmol) in dioxane (5 mL), was refluxed for 12 h, LC-MS confirmed the reaction was competed. The solvent was removed under vacuum. The residue was stirred with toluene for 8 h. Then it was filtered and dried under vacuum to afford the desired N-(2-methylbenzyl)-4,5-dihydro-1H-imidazol-2-amine. LC-MS: m/z=234.0(M+1).

Synthesis of TIC10

7-Benzyl-4-(2-methylbenzyl)-1,2,6,7,8,9-hexahydroimidazo[1,2-a]pyrido[3,4-e]-pyrimidin-5(4H)-one (TIC10)

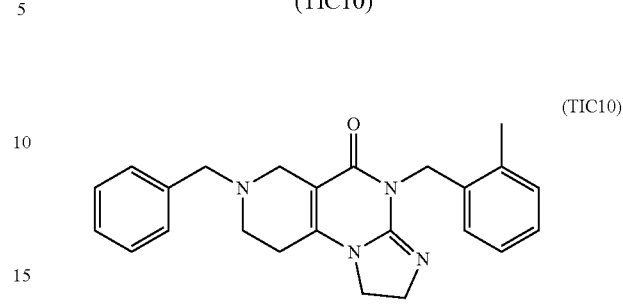

Methyl 1-benzyl-4-oxopiperidine-3-carboxylate (100 mg, 0.4 mmol), N-(2-methylbenzyl)-4,5-dihydro-1H-imidazol-2-amine (128 mg, 0.4 mmol), sodium methyl alcohol (66 mg, 1.2 mmol), was dissolved in methanol (3 mL). The mixture was refluxed for 15 h under $N_2$. LC-MS confirmed the reaction was completed. The mixture was cooled down to room temperature. About half of solvent was removed. Water was added dropwise. Solid came out slowly. The suspension was filtered. The filtered cake was washed with water, dried under vacuum to afford TIC10(30.0 mg, yield 22.1%).

$^1$HNMR (DMSO-d6) δ 2.31 (s, 3H), 2.50-2.56 (m, 2H), 2.65 (m, 2H), 3.04 (s, 2H), 3.63-3.70 (m, 4H), 3.97 (t, J=8.8 Hz, 2H), 4.86 (s, 2H), 6.88 (d, J=6.4 Hz, 1H), 7.1-7.2 (m, 3H), 7.3-7.4 (m, 5H); LC-MS: m/z=387.2(M+1).

EXAMPLE 59

Biological Assay

The disclosed compounds and their pharmaceutically accepted salts are assayed for their anti-cancer activities by the following method.

MTS Cell Proliferation Test
1. Materials
1.1. Compounds and solvents
Samples: the disclosed compounds
Reference compound: TIC10
DMSO was used as the solvent, Cat #8418
1.2. Cell Lines
Two cell lines were used, both HCT116 and MDA-MB-231 were purchased from USATCC.
1.3. Reagents
MTS reagent powder was purchased from Promega. Cat #G1111; PMS from Sigma, Cat #P8625; cell culture medium RPMI-1640, Cat #10040562R; DMEM, Cat #0013CVR; 100× sodium pyruvate solution Cat #136007; 100× Penicillin Streptomycin Solution, Cat ⊇15140122; 100× Penicillin Streptomycin Solution, Cat #15140122; 0.25% Trypsin (Parenzyme), Cat #25200-072; and fetal bovine serum, Cat #16000-044 were all purchased from Life Technologies.
1.4 Instruments
Thermo incubator (Format 371);
Heat force Biosafety Cabinet (HF sage 1500);
BioTek Microplate Reader (Synergy 2).
2. Protocol
2.1 Cell Culture
HTC116 cells were cultured in DMEM complete medium (10% FBS, 100 U/mL Penicillin, 100 ug/mL Streptomycin)
MDA-MB-231 cells were cultured in RPMI-1640 complete medium (10% FBS, 100 U/mL; Penicillin, 100 μg/mL; Streptomycin, 1% sodium pyruvate)

2.2 Preparation of the Test Solution
Solvent: DMSO
Method: the test compounds were weighed and added to DMSO at a concentration of 20 mmol/L, and stored at −80° C.
Considering the solubility of test compounds (DMSO<1%), the following test concentrations (μmol/L) were chosen: 60, 20, 6.67, 2.22, 0.74, 0.25, 0.082, 0.027.
2.3 Procedure of MTS Methods:

Cells at logarithmic phase were harvested, then digested with 0.25% trypsin, and re-suspense in complete growth medium. 150 uL/well of HCT-116 and MDA-MB-231 were dispensed into 96 well culture plates with $2.5 \times 10^3$ cell/well. The plates were pre-incubated in a humidified $CO_2$ incubator at 37° C., 5% $CO_2$) for 24 hours. 50 uL of various concentration of test compounds and reference compound were added. A negative control (only cells and culture medium without compound) and blank control (only culture medium without cells) were set at the same time. The plates were incubated for 72 hr in the incubator. The MTS/PMS solution was prepared and added into 96 well plates according to the test instruction by Promega Corporation. The plates were incubated again for some time, then the absorbance at 490 nm were measured using Biotek Instruments, Inc microplate reader and the cell survival rates calculated.

Cell Survival Rate(%)=(At−Ab)/(Ac−Ab)×100% where,
At=Absorbance value of test compound
Ab=Absorbance value of blank
Ac=Absorbance value of control
3. Results By using GraphPad Prism 5 software, ordinate (y): survival ratio; abscissa (x): drug concentration, the IC50 values were computed and shown in Table 1

TABLE 1

| | Assay Results (IC50: Mean ± SD) | |
|---|---|---|
| No. | HCT116 | MDA231 |
| | IC50 (Mean ± SD) | |
| TIC10 | 1.06 ± 0.24 | 0.79 ± 0.08 |
| I-1 | 0.23 ± 0.009 | 0.24 ± 0.000 |
| I-2 | 0.23 ± 0.004 | 0.24 ± 0.000 |
| I-3 | 0.06 ± 0.006 | 0.07 ± 0.003 |
| I-4 | 1.36 ± 0.023 | 1.17 ± 0.178 |
| I-5 | 5.96 ± 1.346 | 6.81 ± 0.057 |
| I-6 | 4.16 ± 1.508 | 4.45 ± 0.356 |
| I-7 | 2.09 ± 0.092 | 1.88 ± 0.078 |
| I-8 | 1.77 ± 0.230 | 1.82 ± 0.241 |
| I-9 | 0.71 ± 0.001 | 0.74 ± 0.000 |
| I-10 | 2.09 ± 0.016 | 2.19 ± 0.027 |
| I-11 | 1.99 ± 0.041 | 2.18 ± 0.020 |
| I-12 | 2.04 ± 0.029 | 2.07 ± 0.001 |
| I-13 | 1.77 ± 0.072 | 1.94 ± 0.277 |
| I-14 | 1.45 ± 0.155 | 2.08 ± 0.024 |
| I-15 | 0.68 ± 0.003 | 0.73 ± 0.004 |
| I-16 | 2.16 ± 0.013 | 3.07 ± 0.752 |
| I-17 | 2.02 ± 0.022 | 2.14 ± 0.031 |
| I-18 | 2.15 ± 0.022 | 2.21 ± 0.0.15 |
| I-19 | 2.22 ± 0.007 | 3.67 ± 0.036 |
| I-20 | 27.50 ± 3.353 | 27.41 ± 3.237 |
| I-21 | 2.12 ± 0.039 | 2.15 ± 0.034 |
| I-22 | 2.03 ± 0.009 | 2.13 ± 0.008 |
| I-23 | 2.00 ± 0.026 | 2.14 ± 0.025 |
| I-24 | 2.09 ± 0.041 | 1.99 ± 0.039 |
| I-25 | 1.95 ± 0.064 | 1.31 ± 0.154 |
| I-26 | 1.50 ± 0.394 | 2.08 ± 0.067 |
| I-27 | 2.13 ± 0.045 | 2.26 ± 0.018 |
| I-28 | 2.20 ± 0.017 | 2.22 ± 0.029 |
| I-29 | 0.72 ± 0.001 | 0.74 ± 0.002 |
| I-30 | 2.07 ± 0.062 | 2.13 ± 0.005 |
| I-31 | 1.25 ± 0.122 | 1.65 ± 0.050 |
| I-32 | 0.77 ± 0.048 | 0.74 ± 0.001 |
| I-33 | 0.72 ± 0.001 | 0.86 ± 0.136 |
| I-34 | 0.73 ± 0.001 | 0.73 ± 0.002 |
| I-35 | 6.21 ± 0.077 | 4.21 ± 0.634 |
| I-36 | 0.72 ± 0.000 | 0.74 ± 0.001 |
| I-37 | 2.31 ± 0.033 | 2.33 ± 0.095 |
| I-38 | 0.24 ± 0.02 | 0.40 ± 0.03 |
| I-39 | 0.03 ± 0.00 | 0.05 ± 0.00 |
| I-40 | 0.08 ± 0.00 | 0.12 ± 0.01 |
| I-41 | 1.73 ± 0.25 | 2.01 ± 0.01 |
| I-42 | 0.73 ± 0.00 | 1.07 ± 0.01 |
| I-43 | 4.29 ± 0.21 | 2.85 ± 0.77 |
| I-49 | 0.58 ± 0.043 | 0.93 ± 0.098 |
| I-50 | 0.77 ± 0.014 | 1.77 ± 0.429 |
| I-51 | 0.70 ± 0.001 | 0.73 ± 0.004 |
| I-52 | 1.18 ± 0.155 | 2.07 ± 0.115 |
| I-53 | 0.70 ± 0.001 | 0.73 ± 0.002 |
| I-54 | 21.41 ± 0.034 | 24.78 ± 2.580 |
| I-55 | 2.14 ± 0.001 | 2.19 ± 0.039 |
| I-56 | 2.05 ± 0.03 | 2.05 ± 0.04 |
| I-57 | 2.08 ± 0.01 | 2.10 ± 0.07 |

The invention claimed is:

1. A compound of formula (I), imidazole pyrimidine ketones and pharmaceutically acceptable salts thereof, the compound comprising:

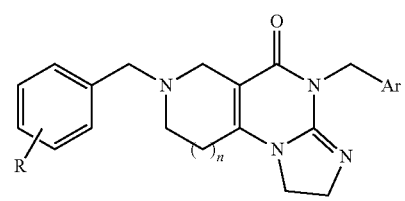

(I)

wherein, n=0 and
R is selected from the group consisting of C1-6 straight-chain or branched-chain alkoxy, and a six-membered heterocyclic ring with one or two hetero atom substitutions;
Ar is selected from the group consisting of mono- or di-substituted aryl groups, with at least one substituent selected from the group consisting of halogen, C1-6 straight-chain or branched-chain alkyl and halo-substituted C1-4 straight-chain or branched-chain alkyl group; or
wherein n=1 and R is selected from the group consisting of and a six-membered heterocyclic ring with one or two hetero atom substitutions;
Ar is selected from the group consisting of mono- or di-substituted aryl groups, with at least one substituent selected from the group consisting of halogen, C1-6 straight chain or branched chain alkyl and halo substituted C1-4 straight chain or branched chain alkyl group.

2. The compound of claim 1, wherein when n=0, said R is further selected from the group consisting of C1-4 straight-chain or branched-chain alkoxy, and an unsubstituted or substituted six-membered heterocycle alkyl;

Ar comprises at least one substituent further selected from the group consisting of C1-4 straight-chain or branched-chain alkyl and halo-substituted C1-4 straight-chain alkyl; and wherein when n=1, said R is further selected from the group consisting of an unsubstituted or substituted six-membered heterocycle alkyl;

Ar comprises at least one substituent further selected from the group consisting of C1-4 straight-chain or branched-chain alkyl and halo-substituted C1-4 straight-chain alkyl.

3. The compound of claim 2, wherein when n=0, said R is further selected from the group consisting of methoxy,

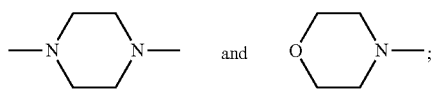

wherein when n=1, said R is further selected from the group consisting of

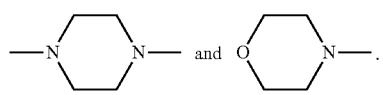

4. The compound of claim 2, wherein, Ar is selected from the group consisting of mono- or di-substituted aryl group and the substituent is one or two groups selected from F, Cl, Br, or one or two methyl or trifluoromethyl.

5. The compound of claim 1, wherein the pharmaceutically acceptable salt thereof is selected from the group consisting of

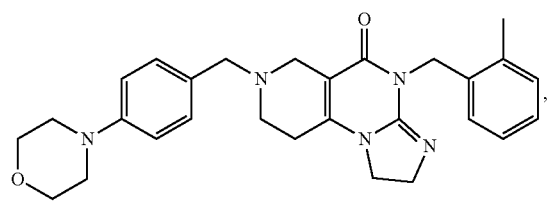

and

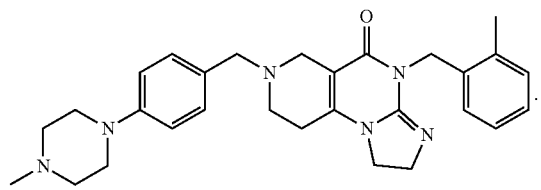

6. A method of preparing a compound of Formula (I), imidazole pyrimidine ketones and pharmaceutically acceptable salts thereof wherein the compound of formula (I):

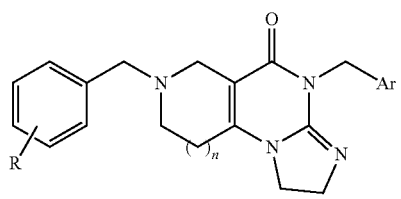

was prepared from compound 6 shown below:

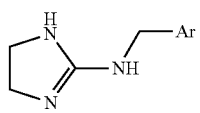

by following the reaction scheme:

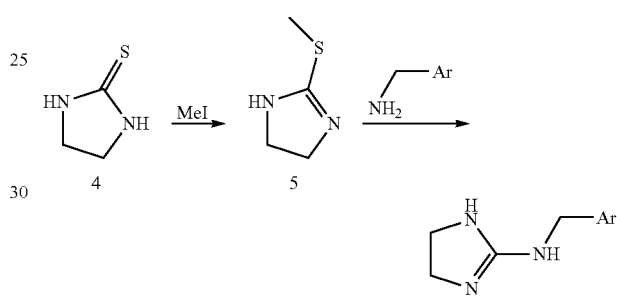

wherein compound 6 reacts with compound 3 to form the compound of Formula (I):

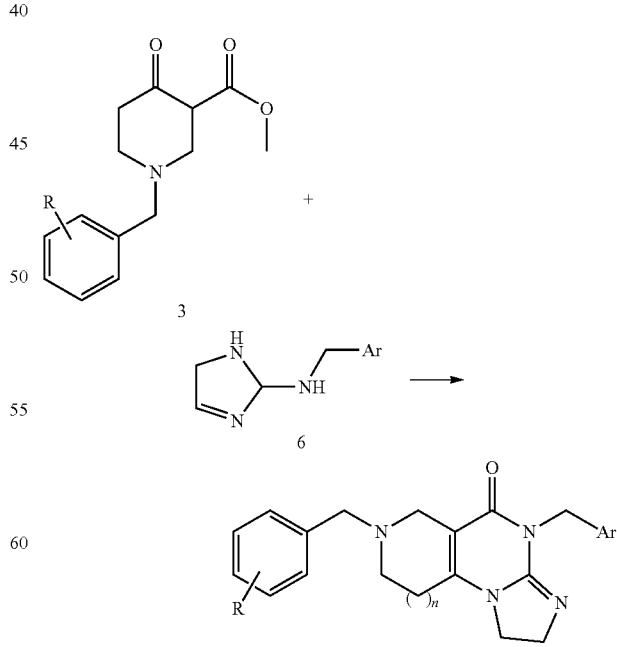

wherein Ar is selected from the group consisting of mono- or di-substituted aryl groups, the substituent include halogen, C1-6 straight-chain or branched-chain alkyl, halo-substituted C1-6 straight-chain or branched-chain alkyl group.

7. The compound of claim 1 wherein the compound is used for the treatment of tumor cells as an anti-tumor agent.

8. The compound of claim 7, wherein said tumor cells are caused by colon cancer or breast cancer.

9. A pharmaceutical composition that contains the compounds from either one of claims 1-5 or pharmaceutically acceptable salts thereof as active ingredients, together with one or more pharmaceutically acceptable excipients.

* * * * *